(12) United States Patent
Fain

(10) Patent No.: US 8,139,833 B2
(45) Date of Patent: Mar. 20, 2012

(54) ANALYZING LARGE DATA SETS USING A COMPUTER SYSTEM

(75) Inventor: Boris Fain, Berkeley, CA (US)

(73) Assignee: Boris Fain, Berkeley, CA (US)

( * ) Notice: Subject to any disclaimer, the term of this patent is extended or adjusted under 35 U.S.C. 154(b) by 523 days.

(21) Appl. No.: 12/421,638

(22) Filed: Apr. 9, 2009

(65) Prior Publication Data

US 2010/0061605 A1     Mar. 11, 2010

Related U.S. Application Data

(60) Provisional application No. 61/043,724, filed on Apr. 9, 2008.

(51) Int. Cl.
*G06K 9/62* (2006.01)
(52) U.S. Cl. ......... 382/128; 382/129; 382/133; 382/159
(58) Field of Classification Search .......... 382/128–133, 382/155–160, 224–228
See application file for complete search history.

(56) References Cited

U.S. PATENT DOCUMENTS

| 5,733,721 | A | * | 3/1998 | Hemstreet et al. | 435/6.14 |
| 2003/0077616 | A1 | | 4/2003 | Lomas | |
| 2004/0002842 | A1 | | 1/2004 | Woessner et al. | |
| 2004/0042646 | A1 | * | 3/2004 | MacAulay et al. | 382/129 |
| 2006/0083418 | A1 | * | 4/2006 | Watson et al. | 382/133 |
| 2008/0020484 | A1 | | 1/2008 | Moon | |

OTHER PUBLICATIONS

Amol et al., "Signal Maps for Mass Spectrometry-Based Comparative Proteomics", MCP papers in press, pp. 7, 10 and figures 1, 4-5, (2003).
Gypi et al., "Quantitative Analysis of Complex Protein Mixtures Using Isotope-Coded Affinity Tags", Nature Biotechnology, vol. 17, pp. 994-999 (1999).

* cited by examiner

*Primary Examiner* — Marcos D. Pizarro
*Assistant Examiner* — Suian Tang
(74) *Attorney, Agent, or Firm* — Stephen J. LeBlanc; Quine Intellectual Property Law Group, P.C.

(57) ABSTRACT

A method and/or system for making determinations regarding samples from biologic sources. A computer implemented method and/or system can be used to automate parts of the analysis.

15 Claims, 21 Drawing Sheets

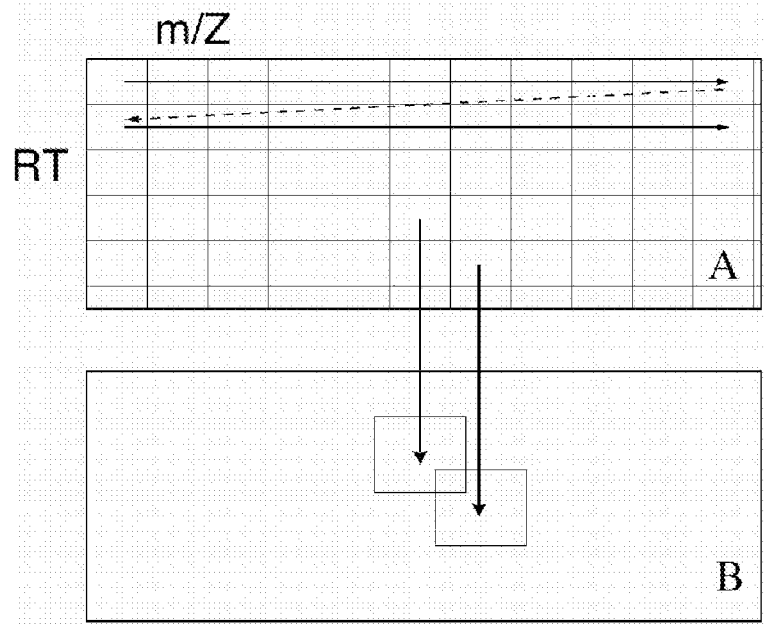
*FIG. 2\*
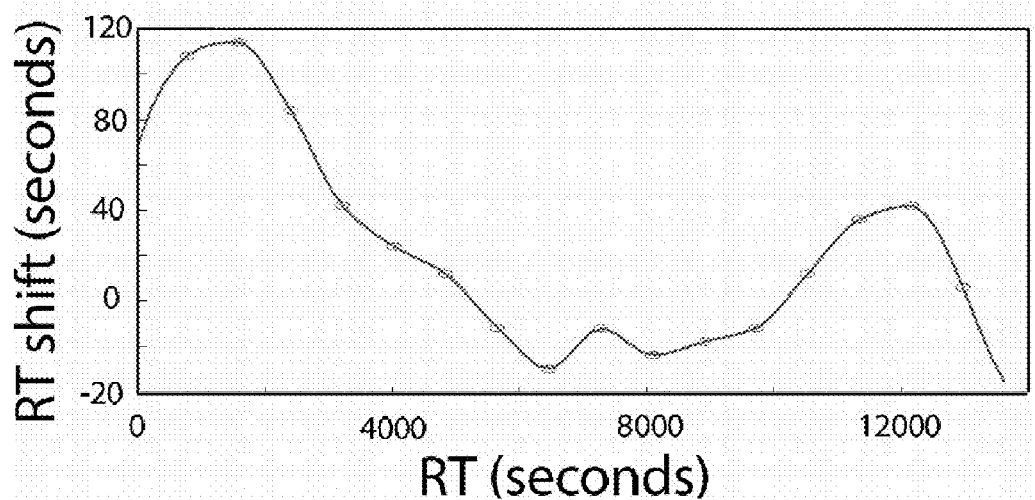
*FIG. 3*

```
function [result] = aggregation(list_name);
MZ_PRECISION = 10;
[Map_file_name, Map_path_name] =
uigetfile('.txt', 'choose list of maps to
aggregate');
list_name = strcat(Map_path_name,
Map_file_name);
[Map_names, designation] =
textread(list_name, '
Full_names = strcat(Map_path_name,
Map_names);
Full_names = strcat(Full_names, '.txt');
Base_names = strrep(Map_names, '.txt', '');
Sparse_names = strrep(Base_names, 'map',
'SMap');
key_name = Sparse_names{1};
Aligned_names = strcat(Sparse_names,
'_alto_', key_name)
for i=1:size(Base_names)
end
tmp = load(key_name); SMap_key =
tmp.SMap; clear tmp;
for i=1:size(Sparse_names)
    tmp = load(Sparse_names{i}); SMap_align
= tmp.SMap; clear tmp;
    shift_name = strcat(key_name,'_',
Sparse_names{i},'_', 'shift');
    'aligning '
    i
    Sparse_names{i}
    shift = align_maps(SMap_key, SMap_align,
shift_name);
    SMap_trans = transform_sparse_map(shift,
SMap_align);
    SMap = normalize_map(SMap_trans,
SMap_key, 1000, 2500, 50000, 80000, 50);
    clear SMap_trans;
    save (Aligned_names{i}, 'SMap');
end
result = 1;
```

```
function [shiftArray] =
align_maps(sparseMap1, sparseMap2,
shift_file_name)
fftw('planner', 'patient');
MZ_LOW = 0000;
MZ_LIMIT = 2000;
rt_size = 2^9;
mz_size = 2^10;
rt_padding = 120;
mz_padding = 100;
mz_overlap = 0;
rt_overlap = 0;
rt_step = rt_size - 2*rt_padding - 1;
mz_step = mz_size - 2*mz_padding - 1;
rt_min = max(sparseMap1.rt_min,
sparseMap2.rt_min);
rt_max = min(sparseMap1.rt_max,
sparseMap2.rt_max);
mz_min = max(sparseMap1.mz_min,
sparseMap2.mz_min) + MZ_LOW;
mz_max = min(sparseMap1.mz_max,
sparseMap2.mz_max) + MZ_LOW;
rt_step = rt_size - 2*rt_padding - 1;
mz_step = mz_size - 2*mz_padding - 1;
Center_Vec = [];
Center = zeros(1,1,2);
rt_end_larger = 0;
num_tiles_rt = 0;
rt_end = 0;
mz_end = 0;
results_array = cell(0);
rt_start = (rt_min + rt_padding:rt_step:rt_max
- rt_padding - rt_size);
rt_end = rt_start + rt_step;
rt_start_larger = rt_start - rt_padding;
rt_end_larger = rt_end + rt_padding;
rt_center = rt_min + floor(rt_start + (rt_end -
rt_start)/2);
[tmp, num_rt_tiles] = size(rt_center);
```

*FIG. 8*

```
mz_start = (1 +
mz_padding:mz_step:MZ_LIMIT -
mz_padding - mz_size);
mz_end = mz_start + mz_step;
mz_start_larger = mz_start - mz_padding;
mz_end_larger = mz_end + mz_padding;
mz_center = mz_min + floor(mz_start +
(mz_end - mz_start) / 2);
[tmp, num_mz_tiles] = size(mz_center);
shift = zeros(num_rt_tiles, 3);
for (i=1:num_rt_tiles)
    clear A B D;
    A = sparse_map_slice(sparseMap1,
rt_start_larger(i), rt_end_larger(i), mz_min,
mz_min + MZ_LIMIT,'filter');
    B = sparse_map_slice(sparseMap2,
rt_start(i), rt_end(i), mz_min, mz_min +
MZ_LIMIT, 'filter');
    C = ones(1 + rt_step + 2*rt_padding, 1 +
mz_step + 2 * mz_padding, num_mz_tiles);
    for (j=1:num_mz_tiles)
        s2 = full(B.map(1:rt_step + 1,
mz_start(j):mz_end(j)));
        s1 = full(A.map(1:rt_step + 2*rt_padding
+ 1, mz_start_larger(j):mz_end_larger(j)));
        if (isempty(s1) | isempty(s2))
            m = 0; n = 0; maximum = 0;
        else
            C(:,:,j)
=(real(ifft2(fft2(sqrt(s1),1+rt_step +
2*rt_padding, 1 + mz_step + 2*mz_padding )
*fft2(...
            rot90(sqrt(s2),2),1+rt_step +
2*rt_padding, 1 + mz_step +
2*mz_padding))));
            C(:,:,j) = 1 + abs(C(:,:,j));
            s1_str = sprintf('
            s2_str = sprintf('
            C_str = sprintf('
    end i
            j
            clear s1 s2;
        end
        Composite = zeros(1 + rt_step +
2*rt_padding, 1 + mz_step + 2 * mz_padding);
        for k=1:num_mz_tiles
            Composite = Composite +
(sqrt(C(:,:,k)));
        end
        clear C D;
        Composite_name =
sprintf('Composite_lim
        [x,y,val] = findlimmax(Composite,
rt_step, rt_step + 2*rt_padding, mz_step,
mz_step + 2*mz_padding );
        x = x - mz_step - mz_padding - 1;
        y = y - rt_step - rt_padding - 1;
        clear Composite;
        shift(i,:) = [x,y,rt_center(i)];
        shift
    clear A B;
end
save(shift_file_name, 'shift');
shiftArray = shift;
[idx, rt_poly, mz_poly, rt_fit_start, rt_fit_stop,
mz_fit_start, mz_fit_stop] = shiftfit(shift, 10);
function
combine_maps_driver(map_list_filename,
skip_vec)
PERMUTE = 0;
RT_INTERVAL = 40;
RAND_CUTOFF = 50;
RT_WIDTH = 5001;
MZ_WIDTH = 150000;
[Map_name, Designation] =
textread(map_list_filename, '
Map_name(skip_vec) = [];
Designation(skip_vec) = [];
tmp = size(Map_name);
```

*FIG. 8 (CONTINUED)*

```
num_maps = tmp(1);
skip_num = skip_vec(1);
tmp = char(Designation);
Designation = tmp;
if (PERMUTE)
    Designation =
Designation(randperm(num_maps));
end
idx_disease = Designation == 'D';
idx_normal = Designation == 'N';
load(Map_name{num_maps});
SMap.map = [];
SMap_disease_mean = SMap;
SMap_disease_std = SMap;
SMap_normal_mean = SMap;
Smap_normal_std = SMap;
SMap_t_test = SMap;
cutoff = SMap.it_cutoff;
RAND_CUTOFF = cutoff;
clear SMap;
rt_min = 1;
rt_max = rt_min + RT_WIDTH - 1;
mz_min = 1;
mz_max = mz_min + MZ_WIDTH - 1;
Disease_mean = sparse(0, mz_max -
mz_min+1);
Disease_dev = Disease_mean;
Normal_mean = Disease_mean;
Normal_dev = Disease_mean;
T_test = Disease_mean;
for (rt_lower=1:RT_INTERVAL:rt_max -
RT_INTERVAL)
    'stop here';
    sandwich = cell(num_maps + 5, 1);
    if (rt_lower > 1500)
        'stop here'
    end for i=1:num_maps
```

```
        load(Map_name{i});
        sandwich{i} =
SMap.map(rt_lower:rt_lower +
RT_INTERVAL - 1, mz_min: mz_max);
        tmp = sandwich{i};
        idx = find(tmp);
        tmp(idx) = tmp(idx) - RAND_CUTOFF;
        sandwich{i} = tmp; clear tmp;
    end
    num_disease = sum(idx_disease);
    num_normal = sum(idx_normal);
    i_disease = 0;
    i_normal = 0;
    disease_array = zeros(num_disease,
RT_INTERVAL, mz_max - mz_min + 1);
    normal_array = disease_array;
    disease_mean_array =
zeros(RT_INTERVAL, mz_max - mz_min +
1);
    disease_dev_array = disease_mean_array;
    normal_mean_array = disease_mean_array;
    normal_dev_array = disease_mean_array;

for (i=1:num_maps)
        if (idx_disease(i))
            i_disease = i_disease + 1;
            disease_array(i_disease,:,:) = log(1 +
full(sandwich{i}));
        end
    end
    disease_array = disease_array;
    disease_mean_array = mean(disease_array,
1);
    disease_dev_array = std(disease_array, 1);
    clear disease_array;
    for (i=1:num_maps)
        if (idx_normal(i))
            i_normal = i_normal + 1;
            normal_array(i_normal,:,:) = log(1 +
full(sandwich{i}));
```

*FIG. 8 (CONTINUED)*

```
        end
    end
    normal_array = normal_array;
    normal_mean_array = mean(normal_array,
1);
    normal_dev_array = std(normal_array, 1);
    clear normal_array;
    [a,b,c] = size(disease_mean_array);
    disease_mean_array =
reshape(disease_mean_array, b,c);
    disease_dev_array =
reshape(disease_dev_array, b, c);
    normal_mean_array =
reshape(normal_mean_array, b, c);
    normal_dev_array =
reshape(normal_dev_array, b, c);
    'stop here' numerator = disease_mean_array -
normal_mean_array;
    denom =
sqrt((disease_dev_array.^2)/num_disease +
(normal_dev_array .^2)/num_normal);
    differential = numerator ./ denom;

differential(isnan(differential)) = 0;
    differential(isinf(differential)) = 0;

clear numerator; clear denom;
    differential(isnan(differential)) = 0;
    differential(isinf(differential)) = 0;
    differential = sparse(differential);
    sandwich{num_maps + 5} = differential;
    clear tmp; clear differential; clear idx;
    clear disease_mean_array; clear
normal_mean_array;
```

```
    clear disease_dev_array; clear
normal_dev_array;
    T_test = vertcat(T_test,
sandwich{num_maps + 5});
    'stop here'
    rt_lower
end
[comb_height, comb_width] =
size(Disease_mean);
rt_gap = RT_WIDTH - rt_lower -
RT_INTERVAL + 1;
if (rt_gap > 0)
bottom = sparse(rt_gap, MZ_WIDTH);
T_test = vertcat(T_test, bottom);
end
SMap_t_test.map = T_test;
if (PERMUTE)
    name1 =
sprintf('SMap_disease_mean_rand2_
    name2 = sprintf('SMap_disease_std_rand2_
    name3 =
sprintf('SMap_normal_mean_rand2_
    name4 = sprintf('SMap_normal_std_rand2_
    name5 = sprintf('SMap_t_test_rand2 _
else
    name1 = sprintf('SMap_disease_mean_
    name2 = sprintf('SMap_disease_std_
    name3 = sprintf('SMap_normal_mean_
    name4 = sprintf('SMap_normal_std_
    name5 = sprintf('SMap_t_test_
end
save(name5, 'SMap_t_test');
'stop here';
function [sparseMap] =
combine_sparse_maps(map_array,
disease_array, method)
function [value] =
compute_array_integral(Arr, factor, threshold)
Arr_thresh1 = factor * Arr;
idx = (Arr_thresh1 > threshold);
```

*FIG. 8 (CONTINUED)*

```
Arr_thresh = (Arr_thresh1(idx));
value = sum(Arr_thresh(:));
tmp = 1;
function [result] =
convert_map_txt_mat(map_file_name)
tmp_str1 = strcat(map_file_name,'.txt');
map = dlmread(tmp_str1);
save(map_file_name, 'map');
result = 'ok'  ;
function [IM, info_struct] =
create_key_map(filename, rt_min, rt_max,
mz_min, mz_max, rt_scale, mz_scale, option)
load(filename);
'loading map slice'
RT_scale = rt_scale;
MZ_scale = mz_scale;
MZ = int32(map(:,2)/MZ_scale);
RT = int32(map(:,1)/RT_scale);
I = (map(:,3));
clear map;
option
[rows,cols] = size(RT);
n = 0;
info_struct = map_info_def();
info_struct.rt_center = rt_min + (rt_max -
rt_min)/2.0;
info_struct.mz_center = mz_min + (mz_max -
mz_min)/2;
info_struct.rt_radius = (mz_max - mz_min);
info_struct.mz_radius = (mz_max - mz_min);
idx = find((RT > rt_min) & (RT < rt_max) &
(MZ > mz_min) & (MZ < mz_max));
X = RT(idx);
Y = MZ(idx);
Z = I(idx);
ttt = size(idx);
length = ttt(1);
RT = X;
MZ = Y;
I = Z;

clear X Y Z;
RT = RT - rt_min + 1;
MZ = MZ - mz_min + 1;
if (strcmp(option, 'limits'))
    IM = sparse(double(RT), double(MZ),
I,floor (rt_max - rt_min + 3),floor (mz_max -
mz_min + 3), length + 10);
end
[rows,cols] = size(IM);
largest_value = max(max(IM));
use_sparse = 1;
if (~use_sparse)
    IM_t = IM';
    idx_tmp = find(filter([1 0.1 1], 2, IM' == 0)
== 1);
    idx = idx_tmp - 1;
else
    IM_t = full(IM');
    idx_zero = find(IM_t == 0);
    idx_zero(1) = [];
    idx_zero(end) = [];
    idx_plus = find(IM_t(idx_zero + 1) ~= 0);
    idx_tmp = idx_zero(idx_plus);
    idx_minus = find(IM_t(idx_tmp - 1) ~= 0);
    idx = idx_tmp(idx_minus);
    'filtering'
    IM_t(idx) = (IM_t(idx - 1) + IM_t(idx + 1))
/ 2.0;
    IM = sparse(IM_t');
    clear IM_t;
end
function [value] =
diagnostic_correlation(SMap, SMap_template)
rt_min = max(SMap.rt_min,
SMap_template.rt_min) + 1;
rt_max = min(SMap.rt_max,
SMap_template.rt_max) - 1;
mz_min = max(SMap.mz_min,
SMap_template.mz_min) + 1;
```

*FIG. 8 (CONTINUED)*

```
mz_max = min(SMap.mz_max,                    mz_overlap = 0;
SMap_template.mz_max) - 1;                   rt_step = rt_size - 2*rt_padding - 1;
rt_min = 500;                                mz_step = mz_size - 2*mz_padding - 1;
rt_max = 3500;                               rt_overlap = 0;
mz_min = 45000;                              Center_Vec = [];
mz_max = 90000;                              Center = zeros(1,1,2);
square1 = SMap.map(rt_min:rt_max,            rt_end_larger = 0;
mz_min:mz_max);                              num_tiles_rt = 0;
square2 = SMap_template.map(rt_min:rt_max,   rt_end = 0;
mz_min:mz_max);                              mz_end = 0;
product = square1 .* square2;                results_array = cell(0);
integral_value = sum(product(:));            shift = zeros(1,3);
tmp = size(square1);                         mzlimit = 100000;
area = tmp(1) * tmp(2);                      while ((rt_end + rt_step + rt_padding) <
value = integral_value / area;           rtmax)
fftw('planner', 'patient');                      clear A a B b C C_blurred;
blur_filt = fspecial('gaussian', 20, 10);        clear mz_conv_info;
for s=12:12                                      mz_conv_info = zeros(1,5);
    for j=16:16                                  rt_start = rtmin + rt_padding +
        file1_num = s                        num_tiles_rt*rt_step;
        file2_num = j                            rt_end = rt_start + (1 + rt_overlap) *
        filename1 = sprintf('map_         rt_step;
        filename2 = sprintf('map_                rt_start_larger = rt_start - rt_padding;
        shift_name = sprintf('                   rt_end_larger = rt_end + rt_padding;
        [rtmina, rtmaxa, mzmina, mzmaxa] =       mz_end_larger = 0;
map_limits(filename1, 3, 10);                    num_tiles_mz = 0;
        [rtminb, rtmaxb, mzminb, mzmaxb] =       mz_end = 0;
map_limits(filename2, 3, 10);                    rt_center = rt_start + rt_step / 2;
        if (rtmina > rtminb) rtmin = rtmina;     [A, a] = create_key_map(filename1,
        else rtmin = rtminb;                 rt_start_larger, rt_end_larger, mzmin, mzmin +
        end                                  mzlimit, 3, 10, 'limits');
        rtmax = min(rtmaxa, rtmaxb);             [B, b] = create_key_map(filename2,
        if (mzmina > mzminb) mzmin = mzmina; rt_start, rt_end, mzmin, mzmin + mzlimit, 3,
        else mzmin = mzminb;                 10, 'limits');
        end                                      while ((mz_end + mz_step +
        mzmax = min(mzmaxa, mzmaxb);         mz_padding) <= mzlimit)
        rt_size = 2^9;                               num_tiles_mz
        mz_size = 2^13;                              mz_start = mz_padding +
        rt_padding = 120;                    num_tiles_mz*mz_step + 1;
        mz_padding = 100;                            mz_end = mz_start + mz_step;
```

*FIG. 8 (CONTINUED)*

```
            mz_start_larger = mz_start -
mz_padding;
            mz_end_larger = mz_end +
mz_padding;
            mz_center = mz_start + mz_step / 2;
            fft_size_rt = rt_end_larger -
rt_start_larger + 1;
            fft_size_mz = mz_end_larger -
mz_start_larger + 1;
            Center_Vec = [Center_Vec
mz_center];
            s2 = full(B(1:1+rt_step,
mz_start:mz_end));
            s1 = full(A(1:1+rt_step +
2*rt_padding,
mz_start_larger:mz_end_larger));
            if (isempty(s1) | isempty(s2))
                m = 0; n = 0; max = 0;
                C = zeros(1 + rt_step +
2*rt_padding, mz_step + 2 * mz_padding);
                s1_str = sprintf('
                s2_str = sprintf('
                C_str = sprintf('
                save(s1_str, 's1');
                save(s2_str, 's2');
                save(C_str, 'C');
            else
                C =
real(ifft2(fft2(sqrt(s1),1+rt_step +
2*rt_padding, mz_step + 2*mz_padding )
*fft2(...
                    rot90(sqrt(s2),2),1+rt_step +
2*rt_padding, mz_step + 2*mz_padding)));
                s1_str = sprintf('
                s2_str = sprintf('
                C_str = sprintf('
                save(s1_str, 's1');
                save(s2_str, 's2');
                save(C_str, 'C');
                [m,n,max] = findmax(C);
            end
            temp_matrix = [mz_conv_info; max,
m, n, rt_center, mz_center];
            mz_conv_info = temp_matrix;
            num_tiles_mz = num_tiles_mz + 1;
            clear s1_raw s2_raw J1 J2 s1 s2 C;
        end
        Composite = ones(1 + rt_step +
2*rt_padding, mz_step + 2 * mz_padding);
        for i=1:num_tiles_mz
            C_name = sprintf('
            load(C_name);
            Composite = Composite .* (sqrt(1 +
C));
        end
        Composite_name =
sprintf('Composite_lim
        save(Composite_name, 'Composite');
        [x,y,val] = findlimmax(Composite,
rt_step, rt_step + 2*rt_padding, mz_step,
mz_step + 2*mz_padding );
        x = x - mz_step - mz_padding - 1;
        y = y - rt_step - rt_padding - 1;
        clear Composite;
        mz_conv_info(1,:) = [];
        mz_conv_info
        num_tiles_rt = num_tiles_rt + 1
        results_array{num_tiles_rt} =
mz_conv_info;
        shift = [shift;[x,y, rt_center]];
        shift
    end
    shift(1,:) = [];
    save (shift_name, 'shift');
end
end
clear all;
RGB = imread('tmp.tif');
I = rgb2gray(RGB);
J = dct2(I);
```

*FIG. 8 (CONTINUED)*

```
imshow(log(abs(J)),[]), colormap(jet(64)),
colorbar
J(1:5,:) = 0;
K = idct2(J);
figure, imtool(I,[0,255]);
figure, imtool(K,[0,255]);
function [M_out, num] = filter_lines(M);
function[factor] = find_norm_factor(SMap,
rt_min, rt_max, mz_min, mz_max,
it_threshold, integral_value)
A = SMap.map(rt_min:rt_max,
mz_min:mz_max);
area = (rt_max - rt_min + 1)*(mz_max -
mz_min + 1);
value0 = compute_array_integral(A, 1,
it_threshold);
desired_value = integral_value;
options = optimset('TolFun', 1e-2, 'TolX', 5e-
2);
y = fzero(@error, [0.1 100], options);
    function y = error(factor)
        y = 1 -
desired_value/compute_array_integral(A,
factor, it_threshold);
    end
factor = y;
end
function [maxX, maxY, maxVal] =
findlimmax(X, col_low, col_high, row_low,
row_high);
temp = X(col_low:col_high,
row_low:row_high);
[a, b, maxVal] = findmax_prot(temp);
maxX = a + row_low - 1;
maxY = b + col_low - 1;
clear temp;
function [maxX, maxY, maxVal] =
findmax_prot(X);
maxVal = max(X(:));
maxX = 0;

maxY = 0;
[Y,I] = max(X);
[Z,I2] = max(Y);
maxX = I2;
[Y,I] = max(X(:,I2));
maxY = I;
A = [9,22,23]
for i=A combine_maps_driver('map_info_combine.csv
', [i])
end
load diseases;
load convolution;
disease = zeros(24, 1);
for (i=1:24)
    if (diseases{i} == 'N')
        disease(i) = 1;
    end
    if (diseases{i} == 'D')
        disease(i) = 2;
    end
end
'stop here'
function [sandwich, matrix] =
load_sample_slice(sample_list_filename,
rt_min, rt_max, mz_min, mz_max)
[Map_name, Designation] =
textread(sample_list_filename, '
tmp = size(Map_name);
num_maps = tmp(1);
rt_interval = rt_max - rt_min + 1;
mz_interval = mz_max - mz_min + 1;
slice = sparse(rt_interval, mz_interval);
sandwich = cell(num_maps, 1);
matrix = sparse(rt_interval * mz_interval,
num_maps);
for i=1:num_maps
    load(Map_name{i});
```

*FIG. 8 (CONTINUED)*

```
sandwich{i} = SMap.map(rt_min:rt_max,
mz_min:mz_max);
    matrix(:,i) = reshape(sandwich{i},
rt_interval * mz_interval,1);
end
'stop here'
function[d_normal, d_disease]=
make_mask(removed_file_num)
RT_INTERVAL = 300;
T_TEST_DIFF = 5;
filename = sprintf('SMap_0
filename1 = sprintf('SMap_disease_mean_
filename2 = sprintf('SMap_disease_std_
filename3 = sprintf('SMap_normal_std_
filename4 = sprintf('SMap_normal_mean_
D_D = 0;
D_N = 0;
load(filename); load(filename1);
load(filename2); load(filename3);
load(filename4);
rt_end = min([SMap.rt_max,
SMap_disease_mean.rt_max,
SMap_disease_std.rt_max,
SMap_normal_mean.rt_max, 3800]);
rt_start = max([SMap.rt_min,
SMap_disease_mean.rt_min,
SMap_disease_std.rt_min,
SMap_normal_mean.rt_min]);
mz_end = min([SMap.mz_max,
SMap_disease_mean.mz_max,
SMap_disease_std.mz_max,
SMap_normal_mean.mz_max, 110000]);
mz_start = max([SMap.mz_min,
SMap_disease_mean.mz_min,
SMap_disease_std.mz_min,
SMap_normal_mean.mz_min]);
for i = rt_start : RT_INTERVAL : rt_end -
RT_INTERVAL - 1
    boundaries = [i, i+ RT_INTERVAL ,
mz_start + 1, mz_end - 1];

i
sample =
SMap.map(boundaries(1):boundaries(2),
boundaries(3): boundaries(4));
disease_mean =
SMap_disease_mean.map(boundaries(1):boun
daries(2), boundaries(3): boundaries(4));
disease_std =
SMap_disease_std.map(boundaries(1):boundar
ies(2), boundaries(3): boundaries(4));
normal_std =
SMap_normal_std.map(boundaries(1):boundar
ies(2), boundaries(3): boundaries(4));
normal_mean =
SMap_normal_mean.map(boundaries(1):boun
daries(2), boundaries(3): boundaries(4));
num_disease = 10;
num_normal = 13;
numerator = disease_mean - normal_mean;
denom = sqrt((disease_std.^2)/num_disease +
(normal_std .^2)/num_normal);
differential = (numerator ./ denom);
clear numerator; clear denom;
tmp = full(differential);
tmp(isnan(tmp)) = 0;
tmp(isinf(tmp)) = 0;
differential = sparse(tmp);
clear tmp;
mask = (abs(differential) > T_TEST_DIFF);
tmp = log( 1 + full(sample));
sample = sparse(tmp);
clear tmp;
dist_disease = abs(sample - disease_mean) ./
disease_std;
idx1 = isnan(dist_disease); idx2 =
isinf(dist_disease);
tmp = full(dist_disease);
tmp(idx1) = 0; tmp(idx2) = 0;
dist_disease = sparse(tmp);
```

*FIG. 8 (CONTINUED)*

```
dist_normal = abs(sample - normal_mean) ./
normal_std;
idx1 = isnan(dist_normal); idx2 =
isinf(dist_normal);
tmp = full(dist_normal);
tmp(idx1) = 0; tmp(idx2) = 0;
dist_normal = sparse(tmp);
dist_d = mask .* dist_disease;
dist_n = mask .* dist_normal;
D_D = D_D + sum(dist_d(:))/sum(mask(:));
D_N = D_N + sum(dist_n(:))/sum(mask(:));
end
'disease';
d_disease = D_D
'normal';
d_normal = D_N
    'stop here'
clear all;
map_list_filename = 'map_info_combine.csv';
[Map_names, Designation] =
textread(map_list_filename, '
Base_names = strrep(Map_names, '.mat', '');
num_mask = 10;
mask_thresh = 5;
extension = sprintf('_masked_cut_
for (i=1:size(Map_names))
    orig_map_name = Base_names{i};
    new_map_name = strcat(Base_names{i},
extension);
    t_test_name = sprintf('SMap_t_test_
    load(orig_map_name);
    load(t_test_name);
    SMap_masked = make_masked_map(SMap,
SMap_t_test, mask_thresh);
    save(new_map_name, 'SMap_masked');
end
function [maskedMap] =
make_masked_map(sparseMap, t_testMap,
t_thresh)
'stop here'
```

```
maskedMap = sparseMap;
mask = (abs(t_testMap.map) >= t_thresh);
maskedMap.map = maskedMap.map .* mask;
idx2 = find(maskedMap.map > 0);
maskedMap.map(idx2) =
log(maskedMap.map(idx2) + 1);
function [rt_min, rt_max, mz_min, mz_max] =
map_limits(filename, rt_scale, mz_scale)
load(filename);
'loaded'
rt_min = min(map(:,1))/rt_scale;
rt_max = max(map(:,1))/rt_scale;
mz_min = min(map(:,2))/mz_scale;
mz_max = max(map(:,2))/rt_scale;
clear map;
function [IM, info_struct] =
create_key_map(filename, rt_radius,
mz_radius,
rt_scale, mz_scale);
load filename;
RT_scale = rt_scale;
MZ_scale = mz_scale;
MZ = int32(map(:,2)/MZ_scale);
RT = (map(:,1)/RT_scale);
I = (map(:,3));
RT_mean = mean(RT)
MZ_mean = mean(MZ)
RT_radius = rt_radius*std(RT)
MZ_radius = mz_radius*std(MZ)
[rows,cols] = size(RT);
X = zeros(rows, 1 );
Y = zeros(rows, 1);
Z = zeros(rows, 1);
n = 0;
metadata_struct = map_info_def();
metadata_struct.mz_start = MZ_mean -
MZ_radius;
metadata_struct.mz_end = MZ_mean +
MZ_radius;
```

*FIG. 8 (CONTINUED)*

```
metadata_struct.rt_start = RT_mean -
RT_radius;
metadata_struct.rt_end = RT_mean +
RT_radius;
for m = 1:rows
    if (((RT(m) > (RT_mean - RT_radius)) &
(RT(m) < (RT_mean + RT_radius))) &
((MZ(m) > (MZ_mean - MZ_radius)) &
(MZ(m) < (MZ_mean + MZ_radius))))
        n = n+1;
        X(n) = RT(m);
        Y(n) = MZ(m);
        Z(n) = I(m);
    end
end
n
X(n+1:rows,:) = [];
Y(n+1:rows,:) = [];
Z(n+1:rows,:) = [];
RT = X;
MZ = Y;
I = Z;
clear X Y Z;
IM = zeros(max(RT) - min(RT) + 1, max(MZ)
- min(MZ) + 1);
RT = RT - min(RT) + 1;
MZ = MZ - min(MZ) + 1;
for m = 1:n
    IM(int16(RT(m)), int16(MZ(m))) =
IM(int16(RT(m)), int16(MZ(m))) + (I(m));
end
[rows,cols] = size(IM);
largest_value = max(max(IM))
for i=2:rows-1
    for j=2:cols-1
        if IM(i,j) == 0
            if (IM(i,j-1) ~= 0) & (IM(i,j+1) ~= 0)
                IM(i,j) = (IM(i,j-1) + IM(i,j+1)) / 2;
            end
        end
    end
    end
    end
display_block(IM);
for i=3:9
    i
    [n, d] = make_mask(i);
    n
    d
end
function [data_mtrx] =
masked_data_array(num_mask, mask_thresh)
map_list_filename = 'map_info_combine.csv';
[Map_names, Designation] =
textread(map_list_filename, '
Base_names = strrep(Map_names, '.mat', '');
t_test_name = sprintf('SMap_t_test_
load(t_test_name);
lin_idx = find(SMap_t_test.map >=
mask_thresh);
data_mtrx = zeros(size(lin_idx),
size(Map_names));
for (i=1:size(Map_names))
    i
    load(Base_names{i});
    data_mtrx(:,i) = SMap.map(lin_idx);
    clear SMap;
end
data_name = sprintf('data_cutoff_
save(data_name, 'data_mtrx');
function error = norm_error(norm_factor,
our_matrix, it_threshold, integral_value)
A_thresh = norm_factor * our_matrix >
it_threshold;
our_integral = sum(A_thresh(:));
error = (integral_value - our_integral)/
integral_valuefunction [SMap_norm] =
normalize_map(SMap, SMap_ref, rt_min,
rt_max, mz_min, mz_max, threshold)
ref_slice = SMap_ref.map(rt_min:rt_max,
mz_min:mz_max);
```

*FIG. 8 (CONTINUED)*

```
value = compute_array_integral(ref_slice, 1,
threshold);
factor = find_norm_factor(SMap, rt_min,
rt_max, mz_min, mz_max, threshold, value)
idx = ((SMap.map .* factor) > threshold);
SMap_norm = SMap;
SMap_norm.map = factor .* (SMap_norm.map
   * idx);
SMap_norm.it_cutoff = threshold;
SMap_norm.it_max = SMap_norm.it_max *
factor;
tmp = size(shift);
num_passes = tmp(1);
rt_center_max = shift(num_passes, 3);
rt_step = shift(2,3) - shift(1,3);
shift_orig = shift;
sigma = std(shift(:,1));
if (sigma < mz_precision)
   sigma = mz_precision;
   mu = mean(shift(:,1));
end
while (sigma > mz_precision);
   mz = shift(:,1);
   mu = mean(mz);
   sigma = std(mz);
   [n,p] = size(mz)
   outliers = abs(mz - mu(ones(n, 1))) >
1.0*sigma(ones(n, 1));
      shift((outliers'),:) = [];
      sigma = std(mz)
end
mz = shift_orig(:,1);
[n,p] = size(mz);
outliers = abs(mz - mu(ones(n, 1))) >
mz_precision;
shift = shift_orig;
shift((outliers'),:) = [];
x_computed = 0:rt_step / 4:rt_center_max +
rt_step;;

plot(shift_orig(:,3), shift_orig(:,1),'Color',
'blue');
hold on;
scatter(shift(:,3), shift(:,1));
mz_poly = pchip(shift(:,3), shift(:,1));
mz_computed = ppval(mz_poly, x_computed);
plot(x_computed, mz_computed, 'Color', 'red');
mean(shift(:,1))
rt_poly = pchip(shift(:,3), shift(:,2));
rt_computed = ppval(rt_poly, x_computed);
figure;
hold on;
plot(shift_orig(:,3), shift_orig(:,2),'Color',
'blue');
scatter(shift(:,3), shift(:,2));
plot(x_computed, rt_computed, 'Color', 'red');
hold off
func_rt = rt_poly;
func_mz = mz_poly;
idx = [0,0];
rt_start = shift(1,3);
rt_stop = shift(end,3);
mz_start = 0;
mz_stop = 10000;
function [sparseMap] = sparse_map(map_col,
rt_scale, mz_scale, filter_flag,...
      original_map_name, disease_name,
type_designation)
sparseMap.rt_scale = rt_scale;
sparseMap.mz_scale = mz_scale;
MZ = uint32(map_col(:,2)/mz_scale);
RT = uint32(map_col(:,1)/rt_scale);
I = map_col(:,3);
MZ = [MZ; 150000];
RT = [RT; 5001];
I = [I; 1];
sparseMap.map =...
   sparse(double(RT), double(MZ), I);
[i,j] = find(sparseMap.map);
sparseMap.rt_min = min(i);
```

*FIG. 8 (CONTINUED)*

```
sparseMap.rt_max = max(i);
sparseMap.mz_min = min(j);
sparseMap.mz_max = max(j);
function [sparseMapSlice] =
sparse_map_slice(sparseMap, rt_min, rt_max,
mz_min, mz_max, filter_flag)
sparseMapSlice.rt_min = rt_min;
sparseMapSlice.mz_min = mz_min;
sparseMapSlice.rt_max = rt_max;
sparseMapSlice.mz_max = mz_max;
sparseMapSlice.rt_scale = sparseMap.rt_scale;
sparseMapSlice.mz_scale =
sparseMap.mz_scale;
sparseMapSlice.map =
sparseMap.map(rt_min:rt_max,
mz_min:mz_max);
sparseMapSlice.it_max =
max(sparseMapSlice.map(:));
switch filter_flag
    case 'filter'
        sliceT = full((sparseMapSlice.map)');
        idx_zero = find(sliceT == 0);
        idx_zero(1) = idx_zero(2);
        idx_zero(end) = idx_zero(end - 1);
        idx_plus = find(sliceT(idx_zero + 1));
        idx_tmp = idx_zero(idx_plus);
        idx_minus = find(sliceT(idx_tmp - 1));
        idx = idx_tmp(idx_minus);
        sliceT(idx) = (sliceT(idx - 1) + sliceT(idx
+ 1)) / 2.0;
        sparseMapSlice.map = sparse(sliceT');
        clear sliceT;
    otherwise
endfunction sp = spdemo(arg1, arg2)
if (nargin ~= 2)
    error('Give order and density');
    return
end
S = sprandn(arg1,arg1,arg2);
F = full(S);

t0=cputime;
B = S * S;
stime=cputime-t0;
t0=cputime;
C = F * F;
ftime=cputime-t0;
sprintf('Order
        arg2, ftime, stime)
function [im_rtb, im_it] =
superposed_images(SMap1, SMap2, rt_min,
rt_max, mz_min, mz_max, filter_type,
filter_size)
load SMap_t_test_1;
pos_values = zeros(33, 1);
neg_values = zeros(11,1);
for (i=0:33)
    i
    tmp = log10(size(find(SMap_t_test.map >
i)));
    pos_values(i + 1) = tmp(1);
end
for (i=10:-1:0)
    i
    tmp = log10(size(find(SMap_t_test.map < -
i)))
    neg_values(11-i) = tmp(1);
end
tmp = log10(size(find(SMap_t_test.map)));
total_values = tmp(1);
vector = [neg_values; total_values;
pos_values];
X = (-10:35)
bar(X,vector);
hold on;
bar(total_values, 'r');
title('Distribution of over and under-expressed
pixels');
xlabel('t-test value between cancer and
normal')
ylabel('Log10 of the number of pixels');
```

*FIG. 8 (CONTINUED)*

```
legend('less than / greater than T', 'total
number')
tmp1 = (shift(2:14,1));
tmp2 = (shift(2:14,2));
mu = mean(tmp1);
sigma = std(tmp1);
[n,p] = size(tmp1);
inliers = abs(tmp1 - mu(ones(n,1),:)) <=
0.5*sigma(ones(n,1),:)
plot(tmp1(inliers));
figure
plot(tmp2(inliers))
txt2oldmap('map_004.txt', 'map_004');
txt2oldmap('map_012.txt', 'map_012');
test_alignment_will
clear all;
load '004_012_shift';
shiftfit(shift, 10);
num_leaveout = 10;
num_components = 3;
t_test_threshold = 10;
[Map_name, Designation] =
textread('map_info_combine.csv', '
full_data =
masked_data_array(num_leaveout,t_test_thres65
hold);
svd_data = full_data;
svd_data(:,num_leaveout) = [];
[U, S, V] = svds(svd_data, 10);
d = diag(S);
figure;
plot(d / sum(d));
[U, S, V] = svds(svd_data, num_components);
coords = full_data' * U;
X = coords(:,1);
Y = coords(:,2);
Z = coords(:,3);
size_vec = 50*ones(size(X));
color = ones(size(X),3);
tmp = char(Designation);

color(:,1) = 0;
color(:,3) = (tmp == 'N');
color(:,2) = (tmp == 'D');
color(num_leaveout,:) = [1,0,0];
figure;
scatter3(X,Y,Z, size_vec, color);
classified_coords_name =
sprintf('Coords_leave_
save(classified_coords_name, 'coords');
function transform_map(shift_file_name,
map1, map2, transformed_name)
load(shift_file_name)
[idx, rt_poly, mz_poly, rt_fit_start, rt_fit_stop,
mz_fit_start, mz_fit_stop] = shiftfit(shift, 10);
rt_scale = 3;
mz_scale= 10;
load(map2_name);
map2 = map;
clear map;
load(shift_file_name);
shift(:,1) = shift(:,1) * mz_scale;
shift(:,2) = shift(:,2) * rt_scale;
shift(:,3) = shift(:,3) * rt_scale;
rt_low = min(shift(:,3)) - 450;
rt_high = max(shift(:,3)) + 450;
[idx, func_rt, func_mz, rt_start, rt_stop,
mz_start, mz_stop] = shiftfit(shift, 30);
map2(:,1) = map2(:,1) -
floor(ppval(func_rt,map2(:,1)));
idx2 = find((map2(:,1) < rt_high) & (map2(:,1)
> rt_low));
map = map2(idx2,:);
clear map2;
save(transformed_name, 'map');
clear all;
function [SMap_t] =
transform_sparse_map(shift_struct, SMap)
[idx, rt_poly, mz_poly, rt_fit_start, rt_fit_stop,
mz_fit_start, mz_fit_stop] =
shiftfit(shift_struct, 10);
```

*FIG. 8 (CONTINUED)*

```
[size_rt, size_mz] = size(SMap.map);
idx_rt = [rt_fit_start:rt_fit_stop];
idx_rt_t = floor(idx_rt + ppval(rt_poly,
idx_rt));
SMap_t = SMap;
SMap_t.map = SMap_t.map .* 0;
SMap_t.map(idx_rt_t,:) = SMap.map(idx_rt,:);
SMap_t.rt_min = idx_rt_t(1);
SMap_t.rt_max = idx_rt_t(end);
tmp = idx_rt_t';
tmp2 = circshift(tmp,1);
tmp3 = tmp - tmp2 - 1;
tmp4 = find(tmp3);
'hello'function txt2mymap(text_filename,
mymap_filename, rt_scale, mz_scale);
M = dlmread(text_filename);
I = floor(M(:,1)/rt_scale);
J = floor(M(:,2)/mz_scale);
v = M(:,3);
clear M;
S = sparse(I,J,v);
save (mymap_filename, 'S');
map = dlmread(filename_txt);
save( filename_mat,'map');
function [SMap] =
txt2sparsemap(txt_file_name, rt_scale,
mz_scale, rt_range, mz_range)
map = dlmread(txt_file_name);
idx = find((map(:,1) > rt_range(1) * rt_scale &
map(:,1) < rt_range(2) * rt_scale) & ...
   (map(:,2) > mz_range(1) * mz_scale &
map(:,2) < mz_range(2) * mz_scale));
SMap = sparse_map(map(idx,:), rt_scale,
mz_scale);
```

*FIG. 8 (CONTINUED)*

ANALYZING LARGE DATA SETS USING A COMPUTER SYSTEM

CROSS REFERENCE TO RELATED APPLICATIONS

This application claims priority from provisional patent application 61/043724 filed 9, Apr. 2008 and incorporated herein by reference.

The above referenced documents and application and all documents referenced therein and all documents referenced herein are incorporated in by reference for all purposes.

COPYRIGHT NOTICE

Pursuant to 37 C.F.R. 1.71(e), applicants note that a portion of this disclosure contains material that is subject to and for which is claimed copyright protection, such as, but not limited to, source code listings, screen shots, user interfaces, or user instructions, or any other aspects of this submission for which copyright protection is or may be available in any jurisdiction. The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

PRECAUTIONARY REQUEST TO FILE AN INTERNATIONAL APPLICATION AND DESIGNATION OF ALL STATES

Should this document be filed electronically or in paper according to any procedure indicating an international application, Applicant hereby requests the filing of an international application and designation of all states. Applicant affirms that Applicant is a United States citizen or entity with rights to file in the United States Receiving office. Should this application be filed as a national application in the United States, this paragraph shall be disregarded.

FIELD OF THE INVENTION

The invention involves a computer implemented method for efficiently classifying a very large data sets as being in one or more classification states, where each classification state is determined from sets of very large training data. More specifically, the present invention relates to the field of analyzing tissue and/or cell samples and/or blood and/or protein and/or other samples or large data sets.

APPENDIX

This application is being filed with appendices. These appendices and all other papers filed herewith, including papers filed in any attached Information Disclosure Statement (IDS), are incorporated herein by reference. The appendix contains further examples and information related to various embodiments of the invention at various stages of development.

Appendix A comprises a scientific paper being submitted for publication discussing various aspects, implementations, and findings related to the present invention. This appendix is fully incorporated as part of the specification. However, as in any academic paper, the description of various aspects of the invention or results of particular experiments may be limited to particular details. Nothing in the paper should be taken to limit the invention except as provided in the attached claims and/or required to overcome prior art.

Permission is granted to make copies of the Appendices solely in connection with the making of facsimile copies of this patent document in accordance with applicable law; all other rights are reserved, and all other reproduction, distribution, creation of derivative works based on the contents, public display, and public performance of the appendix or any part thereof are prohibited by the copyright laws.

BACKGROUND OF THE INVENTION

In a number of fields, complex systems or states are characterized primarily by the large data sets that are generated. In analyzing protein expression from a cell to determine whether that cell is cancerous, for example, a large set of protein expression data from that sample cell is compared with reference data generally consisting of a large set of protein expression data from one or more representative known cancerous cells and a large set of protein expression data from one or more representative known non-cancerous cells. In general, a key goal of systems biology is to investigate complex biological samples, for example at the protein level [1] or gene or DNA or other biologic characteristics levels. Proteomics methods in general and mass spectrometry in particular are offering promise in discovery of potential drug targets and biomarkers [2, 3, 4, 5, 6, 7], and in diagnostic applications [8, 9, 10, 11, 12]. Although the field is blooming, many challenges remain both on the experimental and data analysis fronts [13, 14].

Data analysis of biologic systems is challenging in part due to the large size of raw data sets as well as the exponential nature of processing steps that are required in many data analysis methods to statistically analyze such sets. In some situations, methods useful for analyzing biologic data may have applications in other data analysis areas requiring handling of large data sets.

Typical proteomics processing pipeline consists of the following steps:
 1. Quantization of detector values
 2. Amplitude normalization
 3. Peak Detection and quantification
 4. M/Z and time alignment
 5. Classification and biomarker discovery.

The order of these steps can vary but generally all methods place peak detection before the classification step and most do it before the alignment and normalization steps. See Listgarden and Emili for a review of methods, challenges and approaches to proteomics analysis [15].

More recently, many various strategies and techniques have been proposed for improving and/or automating research and/or diagnostic tests using LC-MS data.

The discussion of any work, publications, sales, or activity anywhere in this submission, including in any documents submitted with this application, shall not be taken as an admission by the inventors that any such work constitutes prior art. The discussion of any activity, work, or publication herein is not an admission that such activity, work, or publication was known in any particular jurisdiction.

REFERENCES

1. T. Ideker, T. Galitski, and L. Hood. A new approach to decoding life: Systems biology. *Annual Review of Genomics and Hitman Genetics*, 2:343-372, 20QL 2. R. Aebersold and M. Mann. Mass spectroscopy-based proteomics. *NAT,* 422:198-207, 2003.
3. A. Prakash, P. Mallick, J. Whiteaker, H. Zhang, A. Paulovich, M. Flory, H. Lee, R. Aebersold, and B. Schwikowski. Signal maps for mass spectrometry-based comparative proteomics. *Molecular & Cellular Proteomics,* 5.3:423-432, 2006.
4. R. Aebersold and M. Mann. Mass spectometry-based proteomics. *Nature,* 411: 198-207, 2003.
5. M. Tyers and M. Mann. From genomics to proteomics. *Nature (London),* 422:193-197, 2003.
6. L. Liotta end E. Petricoin. Molecular profiling of human cancer. *Nat. Rev. Genetics,* 1:48-56, 2000.
7. Diamandis E. P. Mass spectrometry as a diagnostic and a cancer biomarker discovery tool: Opportunities and potential limitations. *Mol Cell Proteomics,* 3:367-378, 2004.
8. K. Yanagisawa, Y. Shyr, B. Xu, P. P. Massion, P. Larsen, B. White, J. Roberts, M. Edgerton, A. Gonzalez, S. Nadaf, J. Moore, R. Caprioli, and D. Carbone. Proteomic patterns of tumour subsets in non-small-cell lung cancer. *Z.a/jcer,.* 362(9382):433-439, 2003.
9. Petricoin E F, Ardekani A M, Hitt B A, Levine P J, Fusaro V A, Steinberg S M, Mills G B, Simone C, Fishman D A, Kohn E C, and Liotta L A. Use of proteomic patterns in serum to identify ovarian cancer. *Lancet,* 59(9306):572-7, 2002.
10. J. T. Wadsworth, K. D. Somers, L. H. Cazares, G. Malik, B. Adam, B. C. Stack Jr., G. L. Wright Jr., and O. John Semmes. Serum protein profiles to identify head and neck cancer. *Clinical Cancer Research,* 10:1625-1632, 2004.
11. B. Wu, T. Abbott, D. Fishman, W. McMurray, G. Mor, K. Stone, D. Ward, K. Williams, and H. Zhao. Ovarian cancer classification based on mass spectrometry analysis of sera, *cancer Informatics,* 2:123-132, 2006.
12. G. Mor, I. Visintin, H. Zhao, P. Schwartz, T. Rutherford, L. Yue, P. Bray-Ward, and D. C. Ward. Serum protein markers for early detection of ovarian cancer. *PNAS,* 102-21:7677-7682, 2005.
13. M. Myers and M. Mann. From genomics to proteomics. *NAT,* 422:193-197, 2003.
14. S. D. Patterson. Data analysis—the achilles heel of proteomics. *Nature Biotechnology,* 21:221-2, 2003.
15. J. Listgarten and A. Emili. Statistical and computational methods for comparative proteomic pro filing using liquid chromatography-tandem mass spectrometry. *Molecular & Cellular Proteomics,* 4.4:419-434, 2005.
16. Wang P., Coram M., Tang H., Fitzgibbon M., Zhang H., Yi E., Aebersold R., and McIntosh M. A statistical method for chromatographic alignment of lc-ms data. *Biostatistics,* Advance Access, 2006.
17. Gygi S P, Rist B, Gerber S A, Turecek F, Gelb M H, and Aebersold R. Quantitative analysis of complex protein mixtures using isotope-coded affinity tags. *Nature Biotechnology,* 17(10):994-9, 1999.
18. Radulovic D., Jelveh S., Ryu S., Hamilton T. G., Foss E., Mayo Y, and Emili A. Informatics plat form for global proteomic profiling and biomarker discovery using liquid-cromatography-tandem mass spectrometry. *Moll. Cell. Proteomics,* 3:984-997, 2004.
19. Nielsen N. P., Carstensen J. M., and Smedsgaard J. Aligning of single and multiple wavelength chromatographic profiles for chemometric data analysis using correlation optimized warping. *J. Chromatogr. A,* 805:17-35, 1996.
20. Bulund D., Danielsson R., Malmquist G., and Markides K. E. Chromatographic alignment by warping and dynamic programming as a pre-processing tool for parafac modelling of liquid chro-matography mass spectrometry data. *J. Chromatogr. A,* pages 237-244, 2002.
21. M. Bellew, M. Coram, M. Fitzgibbon, M. Igra, T. Randolph, P. Wang, D. May, J. Eng, R. Fang, C. Lin, J. Chen, D. Goodlett, J. Whiteaker, A. Paulovitch, and M. McIntosh. A suite of algorithms for the comprehensive analysis of complex protein mixtures using high-resolution lc-ms. *Bioinformatics,* 247:536-540, 2006.
22. F. N. Fritsch and R. E. Carlson. Monotone piecewise cubic interpolation. *SIAMJ. Numerical Analysis,* 17:238-246, 1980.
23. A. Slatnikov, C. F. Aliferis, I. Tsamardinos, D. Hardin, and S. Levy. A comprehensive evaluation of multicategory classification methods for microarray gene expression cancer diagnosis. *Bioinformatics,* pages 631-643, 2005.
24. L. Zhang, W. Zhou, V. E. Velculescu, S. E. Kern, R. H. Hruban, S. R. Hamilton, B. Vogelstein, and K. W. Kinzler. Gene expression profiles in normal and cancer cells. *Science,* 276, 1997.
25. T. O. Nielsen, R. B. West, S. C. Linn, O. Alter, M. A. Knowling, J. X. O'Connel, S. Zhu, M. Fero, G. Sherlock, J. R. Pollack, P. O. Brown, D. Botstein, and M. van de Rijn. Molecular characterization of soft tissue tumors: a gene expression study. *Lancet,* 359:1301-1307, 2002.
26. O. Alter, P. O. Brown, and D. Botstein. Singular value decomposition for genome-wide expression data processing and modeling. *PNAS,* 97-18:10101-10106, 2000.
27. M. E. Wall, A. Rechtsteiner, and L. M. Rocha. Singular value decomposition and principal component analysis. *In A Practical Approach to Microarray Data Analysis,* chapter 5, pages 91-109. Kluwer. Norwell, Mass., 2003.
28. G. H. Golub and C.F. Van Loan. *Matrix Computation.* Johns Hopkins Univ. Press, Baltimore, 3rd edition, 1996.
29. D. A. Notterman, U. Alon, A. J. Sierk, and A. J. Levine. Trancriptional gene expression profiles of colorectal adenoma, adenocarcinoma, and normal tissue examined by oligonucleotide arrays. *Cancer Research,* 61:3124-3130, 2001.
30. Yasui Y, Pepe M., Thompson M. L., Adam B. L., Wright G. L. Jr., Qu Y, Potter J. D., Winget M., Thomquist M., and Feng Z. A data-analytic strategy for protein biomarker discovery: Profiling of high-dimensional proteomic data for cancer detection. *Biostatistics,* 4:449-463, 2003.
31. Randolph T. W. and Yasui Y. Multiscale processing of mass spectroraetry data. *Biostatistics Working Paper Series,* 230, 2004.
32. Baggerly K. A., Morris J. S., Wang J., Gold D., Xiao L. C., and Coombes K. R. A comprehensive approach to the analysis of matrix-assisted laser desorption/ionization-time of flight proteomics spectra from serum samples. *Proteomics,* 3:1667-1672, 2003.
33. P. Du, W. A. Kibbe, and S. M. Lin. Improved peak detection in mass spectrum by incorporating continuous wavelet transform-based pattern matching. *Bioinformatics,* 22-17: 2059-2065, 2006.
34. W. Dubitzky, M. Granzow, and D. Berrar. *Introduction to Genomic and Proteomic Data Analysis.* Springer US, 2007.
35. N. L. Anderson and N. G. Anderson. The human plasma proteome: History, character and diagnostic prospects. Molecular and Cellular Proteomics, 1-11:845-867, 2002.

OTHER REFERENCES

36. ABSOLUTE QUANTIFICATION OF PROTEINS AND MODIFIED FORMS THEREOF BY . . . Microcapillary LC-MS/MS has been used successfully for the large-scale . . . of peptide internal standards by mass-tocharge ratio and retention time in European Patent Document EP1472539
37. BIOMOLECULE CHARACTERIZATION USING MASS SPECTROMETRY AND AFFINITY European Patent Document EP1385998
38. POLYPEPTIDE FINGERPRINTING METHODS, METABOLIC PROFILING www(.)wikipatents(.)com/ca/2370749.html

SUMMARY

The present invention involves techniques, methods, and/or systems for analyzing large data sets (such as those derived from biologic samples or otherwise) and for making a diagnostic or classification and output allowing actions based on the analysis. In specific embodiments, the invention is directed to research and/or clinical applications where it is desired to analyze samples containing varying protein or peptide or other molecules that can be characterized using one or more mass-spectroscopy techniques or other techniques that provide large data sets characteristic of various components of the sample and thereby making a diagnostic or other determination and outputting results or taking an action based on the determining.

The invention is further directed to analyze a biologic or other multi-component sample at a "holistic" level, by classifying a sample into one or more of a limited number of classes using a large data set derived from the sample, but not necessarily attempting to detect specifics of the underlying components of the sample. For example, in an analysis of the protein expression of a tissue or blood sample, a system according to the invention can classify the sample as being either disease or normal based on a large data set representative of protein constituents of a sample but without attempting to identify any particular proteins or peptides in the sample. In many situations, the invention can therefore provide and output a superior diagnostic answer regarding the classification of the sample while avoiding errors and computational complexity that may arise when attempting to identify individual protein or peptide components. In other embodiments, the "holistic" approach to classifying samples may be used as an adjunct and/or to guide various analysis of particular components (e.g., peptides or proteins) of the sample.

In further embodiments, the very fast analysis of a real-time data stream enabled by the invention can be used to identify and/or isolate components (e.g., proteins or peptides) of interest for further analysis during an analysis procedure, e.g., LC-MS. Real-time or near real-time physical component isolation promises to have many applications in research and clinical diagnostic settings. Thus, the analysis of the invention can be used in one or more electronic logic systems as will be understood in the art and a signal thereby used to select physical components in real time.

The invention can also be embodied as a computer system and/or program able to analyze data sets to perform classification and/or analysis as described herein and this system can optionally be integrated with other components for capturing and/or preparing and/or displaying sample data and/or affecting a sample stream during data analysis.

In other embodiments, the computational approach and techniques of the invention can be used to provide important differential and/or diagnostic analysis of essentially any experiment or investigation that produces a large amount of reproducible data arranged in $R^m$ (e.g., Euclidean space). For example, MALDI-TOF (Matrix-assisted laser desorption/ionisation-time of flight) mass spectrometry (MS) data is usefully analyzed by the invention as are large data sets generated by such diagnostic systems as brain and magnetic resonance imaging (MRI) or Computerized Regulation Thermography (CRT) scans.

In one MRI or CRT data application, the invention can be particularly well adapted to finding abnormalities between subjects, or scanning the same person over time to locate a tumor, find out regions of increased activity, or detect other differences in large generated data sets (such as the digital images output by MRI or CRT scans) and present or output such results to a human operator.

Outside of biology and medicine, the invention can be used in such areas as scanning structural elements (e.g., a high performance aircraft wing) using X-ray—to see changes induced by stress. Large map data sets, satellite scans, or astronomical data also may be profitably analyzed according to specific embodiments of the invention.

Various embodiments of the present invention provide methods and/or systems for data classification or diagnostic analysis that can be implemented on a general purpose or special purpose information handling system using a suitable programming language such as Java, C++, C#, Pearl, Python, Cobol, C, Pascal, Fortran, PL1, LISP, MATHLAB, assembly, etc., and any suitable data or formatting specifications, such as HTML, XML, dHTML, TIFF, WIFF, JPEG, BMP, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

Various embodiments of the present invention provide methods and/or systems that can be used to perform a physical transformation. For example, the data analysis of the present invention may be employed in real time systems using Liquid Chromatography-Mass Spectrometry (LC-MS) to segregate samples based on LC-MS results when analyzed as described herein.

Various embodiments of the present invention provide results that are useful, concrete, and tangible. For example, as will be understood from the descriptions herein, analysis according to specific embodiments of the invention can be used on a protein or other biologic sample to provide an output or result indicating whether such sample is from a diseased or normal tissue, which can be used to diagnose conditions such as cancer. In other embodiments, the invention can be used to output data or an image indicating the presence of a tumor from brain or other scanning data. In other embodiments, the invention can be used to output data or an image indicating areas of stress in manufactured products.

The invention and various specific aspects and embodiments will be better understood with reference to the drawings and detailed descriptions provided herein. For purposes of clarity, this discussion refers to devices, methods, and concepts in terms of specific examples. However, the invention and aspects thereof may have applications to a variety of types of devices and systems.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

The invention according to specific embodiments is implemented on special purpose or general purpose logical apparatus, which for simplicity is referred to at times herein as a computer. The definition of "a computer" as used herein should be understood to include, without limitations, any type of information processing apparatus. In general, all such apparatus include, without limitation, one or more mechanisms for logical processing (referred to herein as a processor). All such apparatus include multiple mechanisms for data storage, including volatile and non-volatile electronic memory, magnetic memory (including disk drives), memory closely associated with the processor, such as cache memory, which are collectively referred to herein as storage, and one or more input modules for accessing data, and output modules for outputting results of processor action, including outputting to other machines or mechanisms or outputting to a human operator.

The features and advantages described in this summary and the following detailed description are not all-inclusive, and particularly, many additional features and advantages will be apparent to one of ordinary skill in the art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

When used herein, "the invention" should be understood to indicate one or more specific embodiments of the invention. Many variations according to the invention will be understood from the teachings herein to those of skill in the art.

BRIEF DESCRIPTION OF THE DRAWINGS

FIG. 2 is a diagram illustrating the block nature of an alignment procedure according to specific embodiments of the invention wherein tiles are aligned along an mass/charge (m/z) row. Once the row is finished a consensus process decides on the shift values for that row, and the invention proceeds to the next row further down the retention times (RT) axis. Tiles in map B are made larger than those in A to accommodate shifts.

FIG. 3 illustrates a graph of RT shift vs. RT for a pair of colon samples. The data points are fitted with Piecewise cubic Hermite interpolation (PCHIP), and the resulting function is shown in red. The shift is relatively modest, with a range of 70 seconds.

FIG. 8 is a multi-page figure that sets out selected source code extracts from a copyrighted software program, owned by the assignee of this application, which manifests the invention according to specific embodiments of the invention.

DESCRIPTION OF SPECIFIC EMBODIMENTS

Overview

In the context of the invention, it has been determined that the peak detection step of earlier methods is one cause of analysis error. These errors have been found to get worse with increasing complexity. Some approaches have tried to address this problem by the simplification the peptide mixture before running the mass spectroscopy (MS) experiments [17].

According to specific embodiments of the invention, the invention in important respects performs analysis on raw data directly and thus avoids feature detection errors that can arise in complex mixtures as well as the often unreliable peak matching for RT alignment. In specific embodiments, detecting features, can be performed either: (1) after the complexity of the data has been reduced in a natural way, for example, by considering only signals with certain degree of statistical separation between cancer and normal tissue, or (2) by using statistical ensemble information.

Figure 1:
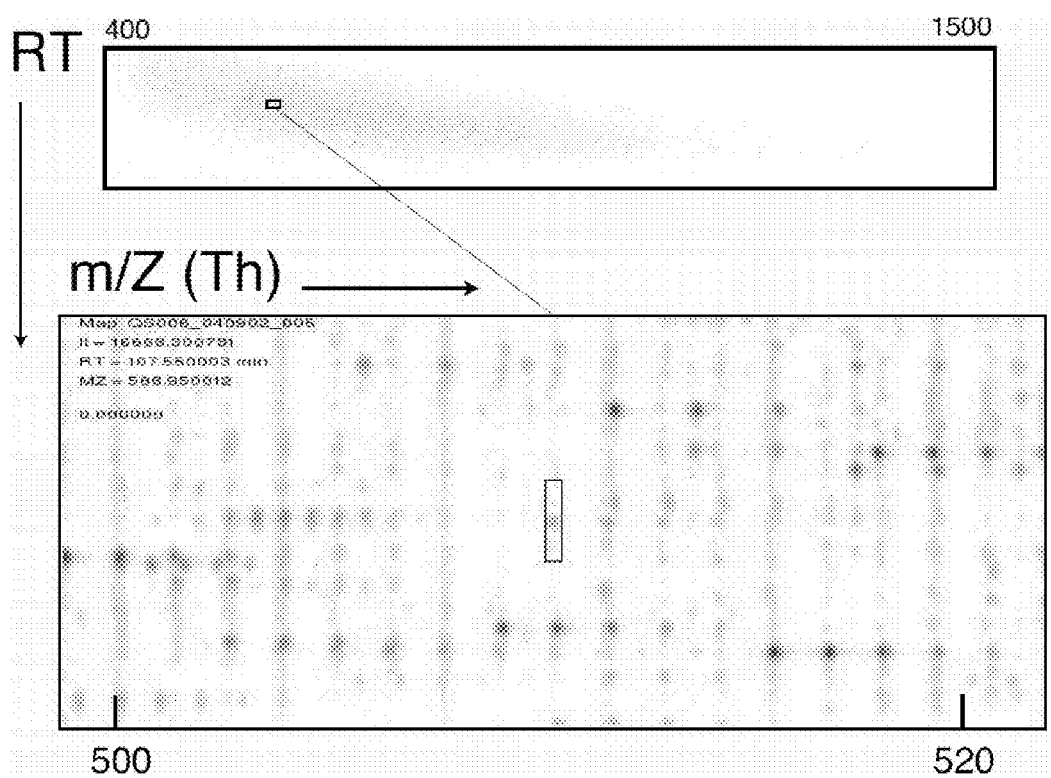
FIG. 1 is a diagram showing an image representing Liquid Chromatography-Mass Spectrometry (LC-MS) results that are analyzed to make a determination according to specific embodiments of the invention. The upper rectangle is an overview of a full image or map, and the lower rectangle is an image of a small subset. A cluster of equally spaced carbon isotope spots going from left to right is a signature of a peptide. The vertical streaks are likely constantly eluting components. Such streaks are filtered out prior to further analysis according to specific embodiments of the invention.

According to specific embodiments of the invention, proteomics data is analyzed generally in the following order:
Quantization of detector values into images
Image (or Map) alignment
Image (or Map) normalization (optional) Statistical feature detection
Selection of differential signals
Statistical data reduction
Discrimination (also referred to as diagnoses) or Classification
Output of discrimination results Representation and Quantization of Maps FIG. 1 is a diagram showing an image representing Liquid Chromatography-Mass Spectrometry (LC-MS) results that are analyzed to make a determination according to specific embodiments of the invention. The upper rectangle is an overview of a full image or map, and the lower rectangle is an image of a small subset. A cluster of equally spaced carbon isotope spots going from left to right is a signature of a peptide. The vertical streaks are likely constantly eluting components. Such streaks are filtered out prior to further analysis according to specific embodiments of the invention. In particular examples described herein, data used can be understood as a list or array or image of m/z and RT values. In particular example embodiments, the original MS output .WIFF files are first converted to a set of triples containing values for RT, m/z and intensity (I).

In particular implementations, to induce sparseness, values below a cutoff of 10 counts are considered to be zero. Typical image maps analyzed according to specific embodiments of the invention contain approximately $1 \cdot 10^7$ to $5 \cdot 10^7$ out of a possible $5 \cdot 10^8$ entries, making them 2%-10% sparse. In particular implementations, proteomics maps are stored as sparse matrices (or images) with float entries. As int16 only cover a 64K range, choosing float over int32 does not increase storage requirements and provides a virtually unlimited dynamic range. In particular embodiments, row indices are linearly related to RT values, and the column indices to m/z. When choosing appropriate RT and m/z scales to convert the triplets into images, it has been found desirable for scale(s) to be small enough to make the image smooth and to reduce storage requirements, but not so small as to lose information to the point of actually dropping isotope clusters (See FIG. 1 for an illustration. All Figure references, unless otherwise indicated, refer to the figures of Appendix A).

Various techniques to determine quantization scales may be employed, as would be understood in the art, described elsewhere in this submission, and as appropriate for particular data sets.

Alignment

An important bioinformatics challenge in LC-MS analysis is the alignment of RT and, to a lesser extent, m/z data across multiple samples (see, inter alia, pp. 424-426 of Listgarten et. al [15] and section 2.2 of Wang et. al. [16] for summaries. See, also, methods described in [18, 19, 20, 21, 3].) The present invention operates so as to avoid peak detection as much as possible and therefore, according to specific embodiments of the invention, the invention aligns raw data directly. The invention does not assume any functional form for the shifts from sample to sample, but allow them to vary in an arbitrary way. Because m/z calibration is usually very good, in particular embodiments the invention uses the assumption that the deviations in m/z are relatively small compared to those in the RT dimension(s). FIG. 2 is a diagram illustrating the block nature of an alignment procedure according to specific embodiments of the invention wherein tiles are aligned along an mass/charge (m/z) row. Once the row is finished a consensus process decides on the shift values for that row, and the invention proceeds to the next row further down the retention times (RT) axis. Tiles in map B are made larger than those in A to accommodate shifts.

FIG. 3 illustrates a graph of RT shift vs. RT for a pair of colon samples. The data points are fitted with Piecewise cubic Hermite interpolation (PCHIP), and the resulting function is shown in red. The shift is relatively modest, with a range of 70 seconds. To better understand alignment according to specific embodiments of the invention, consider aligning one image, A, to another, B. The invention computationally divides A into tiles and B into corresponding slightly larger overlapping tiles. Tiles Bij exceed tiles Aij generally by at least the expected amount of m/z and RT fluctuations, or of other mapped data fluctuations when analyzing other types of data.

In an example alignment, the invention proceeds row by row, focusing on a particular RT range. For each row k, the invention zero-pads the Aij to match Bij and computes the 2-D correlation using an FFT as described herein. The optimal superpositions correspond to maxima of Fkj.

In an example embodiment, to eliminate multiple maxima and uncover possible m/z variations, the invention performs a consensus procedure for the whole strip k.

Superposing all the Fkj for the row with slight local m/z perturbations and the true maximum is the one that 'shines through' all the F's for this row. The consensus procedure was also done via the 2-D FFT correlation. The invention can handle miscalibrated m/z experiments, as well as RT shifts which depend on m/z. Backtracking the consensus row maximum to each Fkj provides a grid of values for m/z and RT shifts for the row k. The grid of shifts is extended to a continuous range of values by a suitable approximation technique, for example, PCHIP [22] in specific embodiments, though other approximate techniques can be used.

In some situations, RT shifts generally have irregular functional forms. With the RT and m/z alignments in hand, transform map A to align with map B. Filters may be applied once again to remove artifacts produced by roundoff errors.

In further embodiments, occasionally—usually at the edges of maps—a definitive alignment is difficult because there are not enough distinctive spot constellations to match up the patterns. In general, the invention may determine not to align edge regions simply because there is not much information to align and leave them out of the analysis. When such cases surface in the interior of a map, the invention uses the value interpolated (e.g., by PCHIP) from neighboring aligned tiles.

Generally, to align a whole series of maps, the invention first selects a key map and aligns and transform every other map in the collection to it. An alignment is considered successful in example embodiments if corresponding isotope clusters overlap, with their centers less than 2 standard deviations apart. Thus the natural size of our precision requirement for alignment is the width of a typical peptide spot (FIG. 2). If such overlap is difficult to achieve, a suitable blurring filter can be applied to the images.

According to specific embodiments of the invention. the use of the FFT (in 2, 3, or more dimensions) makes alignment very fast, but it also imposes certain requirements on the variability of the data. The RT variability—the change in shift—over an alignable tile region (regions are 5 min wide in our case) has to be less than the width of a peptide spot (typically 15-50 seconds). If the variability is greater than this, one can either make the tiles narrower or start using morphological operations (i.e. shrinking, stretching, etc.). Morphological operations are costly, as most will require a repeat of the FFT. Since we compound alignment information over the whole m/z range, we can and prefer to narrow the RT swaths.

Further analysis has suggested that the invention is better able to align proteomic maps because of a large enough proportion of the isotope clusters on the maps are in a very specific biologically determined configurations relative to each other. Because of the high sensitivity of the FFT and the small likelihood of dissimilar peptides being distributed in coordinated patterns, alignment across tissues is expected to be possible. It will be understood to those of skill in the art that other data sets, such as certain MRI scan data or captured satellite data or astronomical data, will have a similar large enough proportion of data clusters or patterns in a very specific externally determined configurations relative to each other and therefore alignment according to specific embodiments of the invention will be effective in these other areas.

Normalization

Because LC-MS experiments, like many other data capture situations, suffer from systemic variation in both overall and local abundance measurements, it is generally necessary to normalize all intensities. According to specific embodiments of the invention, the invention normalizes the raw data after the maps are aligned. An underlying assumption that informs the invention in specific embodiments is that the overall abundance of everything coming through the apparatus should be equal across experiments.

While a wide variety of normalization techniques are know in the art and can be employed according to specific embodiments of the invention. a particular example technique is described herein. The first step is a global normalization of the samples: find a multiplier for each map that makes the total integral of all signals (i.e. the volume under the full image) equal across the whole collection. This procedure may be slightly involved where an intensity threshold is used to make maps sparse: when all map values are multiplied by a constant this also changes the threshold which must then be readjusted. A minimization routine is used that at each step multiplies the map by a constant, resets the threshold, computes the integral, and then tries to make the final answer equal to that of a reference map. Generally, the procedure converges in 3-6 steps. To check for local intensity variations perform the same procedure on several rectangular sub-regions of the maps, and then fit a local grid of normalization coefficients with PCHIP or comparable computation.

Analysis

Figure 4:
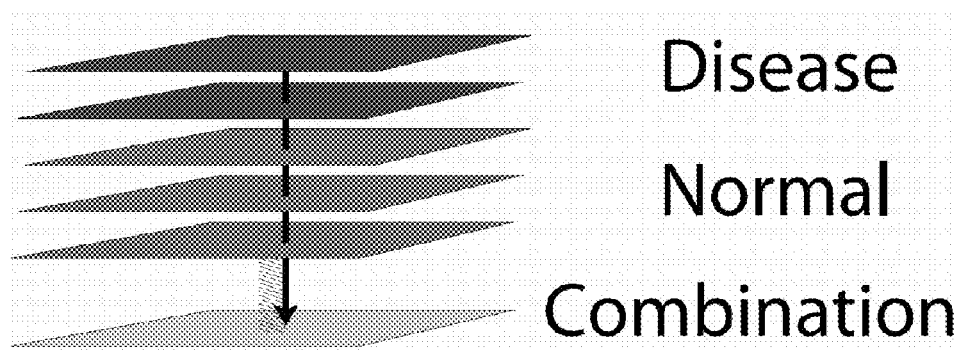
FIG. 4 illustrates a method according to specific embodiments of the invention wherein once the maps (or images) are aligned, the invention performs pixel-by-pixel operations across the data collection.

FIG. 4 illustrates a method according to specific embodiments of the invention wherein once the maps (or images) are aligned, the invention performs pixel-by-pixel operations across the data collection. The resulting collection of aligned and normalized proteomics maps represented as images (e.g., in FIG. 4) generally contains all the information produced in the lab. The invention can now perform pixel-by-pixel operations across the proteome of a particular disease.

As a particular example, and to better illustrate operation of the invention, usefulness of such whole-proteome image operations is illustrated by performing two key proteomics analysis tasks: differential biomarker analysis, and disease diagnostics. In the following sections all intensities have been transformed to their natural logarithms.

Statistical Feature Detection

In this example, each map contains approximately $1 \cdot 10^7$ non-zero points. It is difficult to statistically analyze this much data with currently available computational resources. Dissimilarity filtering of t=1 and lower does not filter out enough points to make computation tractable. To reduce dimensionality, the invention utilizes the following observation: many of the pixels' expression levels are necessarily highly correlated—most glaringly, ones comprising the same feature signature. Such pixels lie along similar m/z ranges. Thus, the invention reduces the dimensionality of the data sets by performing an SVD transformation of each 20-pixel-wide MZ stripe into e.g., 22 (the number of samples in this example) principal components' expression levels. This could be thought of as a sample-collection statistical feature detection. This operation is only performed for analyses containing differential expression of t>1. Higher t-test filter levels reduce the data sufficiently without the need for statistical feature reduction.

Differential Expression

Figure 5:
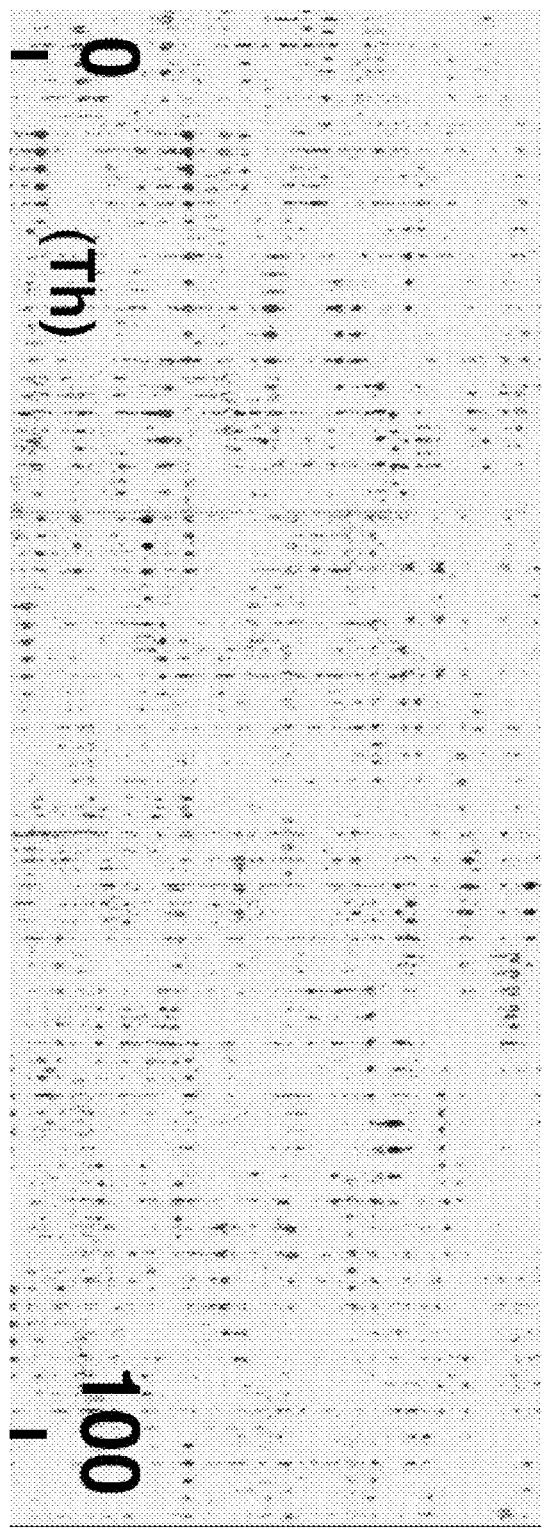
FIG. 5 is an illustrates a rectangular subset of a differential image, showing only pixels that are overexpressed in cancer. The intensity of each pixel is proportional to the statistical measure of difference (T test) between the disease and normal samples' distributions for each pixel. At least five strong differentials are seen in this example.

At this point, the invention proceeds in a way that will be understood to those familiar with handling of a very large (e.g., $10^7$) microarray experiment. As an example, to separate normal from cancer tissue, focus on peptides which are differentially expressed between the two groups [23], To perform differential filtering using image processing, first compute four new pseudo-maps: (1) disease mean, (2) disease deviation, (3) normal mean and (4) normal deviation. All four are images just like the original maps. The statistical pseudo-maps are produced by performing a pixel-by-pixel statistical operation (e.g., in FIG. 4) producing at each pixel a mean or standard deviation (stdev) of the corresponding log-normal pixels in the disease and normal 'pancakes'.[3] Then produce a fifth pseudo-map, the t-test map, each pixel of which is the t-statistic of the disease and normal distributions for the corresponding pixels. FIG. 5 is an illustrates a rectangular subset of a differential image, showing only pixels that are overexpressed in cancer. The intensity of each pixel is proportional to the statistical measure of difference (T test) between the disease and normal samples' distributions for each pixel. At least five strong differentials are seen in this example. The figure shows five strong differentials in a tile 14 minutes by 20000 Da/e.

According to specific embodiments of the invention, noise, contamination streaks and spurious signals dissolve in the statistical synthesis, leaving behind clear peptide fingerprints. Because the differential map is considerably cleaner and sparser than the individual maps which were used to compute it, at this stage, standard feature-detection algorithms where desired can be effectively employed.

Reversing the alignment corrections enables tracing the isotope clusters of interest back to their original maps.

Figure 6:
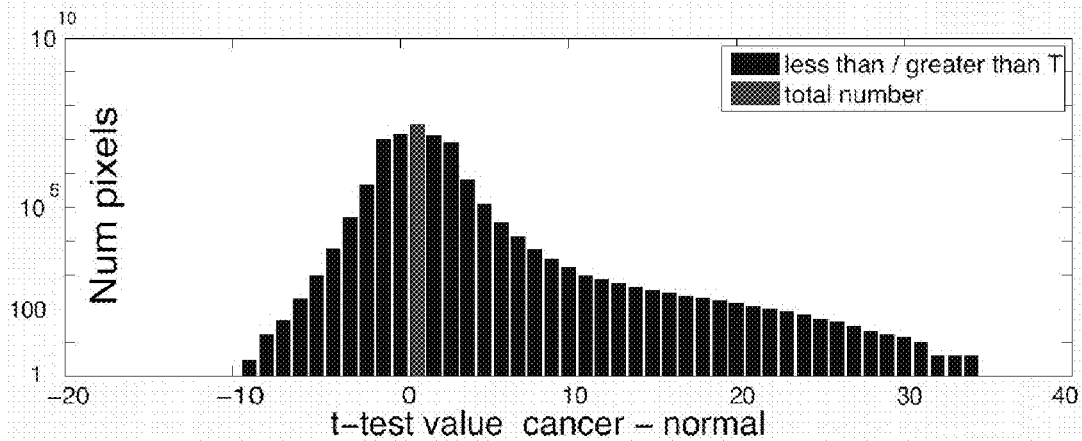
FIG. 6 is a block diagram showing the distribution of cancer/normal over/underexpressed signals. The y-axis scale is logarithmic. The height of each bar is equal to the number of pixels that have a statistical difference between cancer and normal intensity distributions greater than its x-axis t-value. The bar at 0 shows the total number of nonzero pixels. The bars to the left of 0 correspond to underexpressed signals, and the ones on the right are overexpressed.

To examine the proportion of peptides over and under-expressed in cancer tissue, FIG. 6 illustrates the log base 10 logarithm of the number of pixels that remain for each level (t-test) of over/under expression. The red bar represents the total number ($<<3 \cdot 10^7$) of signals! One interesting observation is that more proteins are over-expressed than under-expressed in cancer. Another is that there is relatively little of each: from this point on we shall be working with <0.001% (\t\>5) of the total. Colon tissues, it seems, are not very different from each other even in malignancy. This result correlates with comparable large-scale gene expressions studies [24]. The small proportion of differential signals underscores the importance [23] of filtering away the rest to perform diagnostic analysis.

Once a suitable statistical cutoff has been chosen, the invention further filters the datasets by a differential mask. The mask is a b/w (or opaque/transparent) image in which the transparent pixels correspond to regions which have a minimum of a specified degree of statistical difference between cancer and normal.

Tumor Classification and Expression Levels Variation.

Another central aim of proteomics is diagnosis of disease. In addition to many studies that used gene expression to classify tumors (e.g. [25]), several groups have pursued similar aims with proteins. For example, Yanagisawa et. al. [7] achieved considerable success with non-small-cell lung cancer tumors, Petricoin et. al. [8] classified breast cancer cases from serum information, Wadsworth et. al. [9] investigated serum from head and neck cancer patients, and Mor et. al. [11] correlated results from protein microarrays with epithelial ovarian cancer. A common thread in these works is the selection of a very small (npeaks≦$10^2$) subset of the proteome, as well as the complexity of the decision process.

The present invention, in contrast, does not search for 'smoking gun' biomarker(s) to classify malignancies, but instead generally examines a large subset of the proteins and analyses and combines the statistical signals from the whole set.

FIG. 6 is a block diagram showing the distribution of cancer/normal over/underexpressed signals. The y-axis scale is logarithmic. The height of each bar is equal to the number of pixels that have a statistical difference between cancer and normal intensity distributions greater than its x-axis t-value. The bar at 0 shows the total number of nonzero pixels. The bars to the left of 0 correspond to underexpressed signals, and the ones on the right are overexpressed. In particular experimental work, we have <<$5\cdot10^7$ pixels/signals, and <<$5\cdot10^4$ after differential filtering (\t\>5, FIG. 6). Many of these must be highly correlated—for example, the pixels composing a single spot or pixels from different charge-states of the same peptide clearly are. Statistically, we proceed in the spirit of large-scale DNA microarray studies [25, 26, 27], with the complication of having 1,000 times more signals ($5\cdot10^7$K vs. 44K).

In a sense, the invention can be understood as performing feature detection, but these features are not the expected peptide fingerprints, but rather statistical principal eigenfeatures with respect to (w.r.t.) the collection of samples. This clearly merges pixels belonging to the same peptide, but it also combines peptides belonging to the same protein, as well as groups of proteins with highly correlated (across the collection) expression levels.

Although dimensional reduction is important, a simple PCA is generally intractable because the covariarice matrix is unmanageable at about $10^{12-18}$ entries. As in [27], principal components are determined by using Singular Value Decomposition (SVD) [28, 27] on the data matrix. With 22 samples in the discussed example, data matrix A has (m, n) dimensions of $5\cdot10^4\times22$ after differential sparseness reduction: quite manageable for SVD. While the invention in this example provides only have 22 eigenfeatures, as in [26], it is expected the first few components to dominate the statistical variance of the data.

Classification proceeds as follows: use leave-one-out cross-validation to access performance. First align and normalize all samples, and apply a |t|>5 differential mask to the 'unknown' map, as well as to the collection of 21 'known' maps. Then form a m×n (n=21) data matrix A by concatenating the remaining non-zero values from the 21 maps. Use $SVD^4$ to decompose the data matrix as A=$USV^T$ (dim(s)=21× 21) and isolate the 21 columns of U as the new basis vectors for the feature space. Then project the unknown sample onto the eigenfeatures {m} to obtain its new coordinates. FIG. 11 in the supporting information section shows the proportion of variance accounted for by each principal component. Repeat the procedure 22 times each time obtaining the coordinates of a different 'unknown' sample. As desired, most of the variation is captured in the first few principal components: 58% in the first two, 75% in the first three, and 82% in the first four (see FIG. 11 for a graphical summary of the eigenfeatures' contribution to overall variance).

Figure 7:
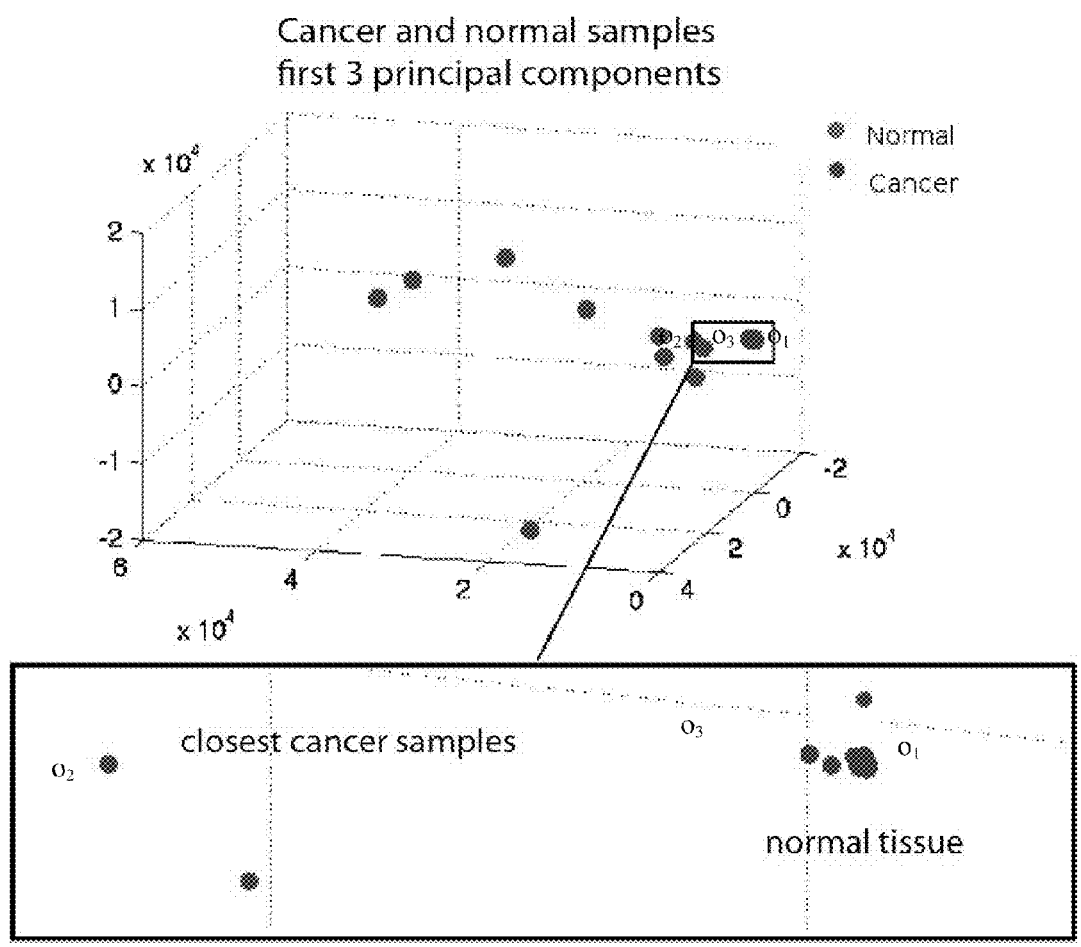
FIG. 7 illustrates an example output showing cancer and normal samples' locations in the first 3 principal eigenfeatures' basis. The 3D representation contains 75% of the variation and is sufficient for visual explanation of the relative arrangement of the samples. In this example, the normals form a tight cluster near the origin; the cancers are scattered throughout the space and are not well clustered in comparison. The lower rectangle is a magnification of region around the normal cluster. It provides an enhanced view of the separation between the normals and nearest cancers. The closest cancer point is eight (8) standard deviations away from the normal cluster.is The hollow sample points, $o_1$, $o_2$ and $o_3$, represent three different samples mapped into such a space and output as normal, cancerous, and undetermined, respectively.

FIG. 7 illustrates an example output showing cancer and normal samples' locations in the first 3 principal eigenfeatures' basis. The 3D representation contains 75% of the variation and is sufficient for visual explanation of the relative arrangement of the samples. In this example, the normals form a tight cluster near the origin; the cancers are scattered throughout the space and are not well clustered in comparison. The lower rectangle is a magnification of region around the normal cluster. It provides an enhanced view of the separation between the normals and nearest cancers. The closest cancer point is eight (8) standard deviations away from the normal cluster.is The hollow sample points, o1, o2 and o3, represent three different samples mapped into such a space and output as normal, cancerous, and undetermined, respectively. This output can be produced on a computer screen or printed output to allow a user to see the classification basis of one or more samples (e.g., sample points, $o_1$, $o_2$ and $o_3$). In addition, or alternatively, the invention may output only a textual score or result regarding a sample, such as:

$o_1$ normal;

$o_2$ cancerous;

Using the invention, there is no need for complicated machinery such as SVM or NN [25, 11]. The distribution of samples according to protein expression levels is a very interesting result. Our observations are consistent with previous expression studies [29] but we are now looking at proteins themselves. First we see that colon tissues are mostly the same (FIG. 6). Second, in the differences between normal and disease, the normals are, again, very similar. The cancers, however, are significantly more diverse (FIG. 7). This finding brings important implications to the search for treatment targets and diagnostic biomarkers.

Proteomic Data Processing

A bioinformatics pipeline according to specific embodiments of the invention has many desirable properties. The invention is generally faster than the machine generates data and scale linearly with the number of samples. The invention has been experimentally shown to easily handle the peptide density of about $5\cdot10^4$ peptides, and can absorb at least 2 orders of magnitude increase in complexity without increasing image size and resolution. After that the storage and computational requirements will increase linearly.

The approach of the invention is holistic in the sense that the invention uses all the information available from the experiment and treats the LC-MS data as one large signature. The invention can therefore bypass or delay one of the major sources of error in data processing—peak detection. Imagine an extreme case of increasing the peptide density in FIG. 2 until there are no areas of white. Peak detection would fail, but the invention will align and tease out differential and diagnostic information from the maps.

The invention, in a very natural way, easily operates on large subsets of the proteome, such as the differentials' subset. Operations and parameters arise from the data itself: for instance, the main units of relevant scales are the width of a peptide spot and peptide density. Because the invention keep all the data the integrity of the final analysis is much improved. For example, in the present invention, the much-maligned 'missing' values [34] correspond to actual null intensities and can be reliably treated as such.

In LC-MS data sets, the invention accommodates arbitrary variations in retention time(s) and even in m/z calibration without using spiked standards. The alignment procedure lends itself easily to quality control and examination because every step can be checked visually. As will be understood in the art, the invention is naturally extendable to three or more dimensions.

As discussed above, the performance, integrity, and complexity handling of the invention make is immediately useful in current LC-MS analysis tasks. Additionally, the invention's speed and precision also makes it possible to inject bioinformatics directly into the experimental pipeline. One possible application is to align a running sample to a collection of previously run samples on the fly during elution through the column. One can then predict the exact locations of peptides of interest, and send them to MS-MS identification with good precision.

Differential Expression and Tumor Classification

To illustrate applications of our the invention, as an example, we analyzed the colon cancer set for differential expression, and classified tumors into proper cancer and normal sets. The invention allowed us to uncover a very interesting result: at the protein level tumors show a much greater level of diversity than normal tissue. This finding has important implications for therapeutic and diagnostic efforts.

Thus, according to specific embodiments, the methods of the invention illustrate that when one gives up the desire to chemically identify the peptides and proteins involved in a process of interest, one gains the ability to manipulate, sort, correlate and distinguish sets of virtually unlimited numbers of protein expression levels. Clustering and classification according to the invention is effective even in cases where the density of information will render ms/ms peptide identification impossible. This is supported experimentally by how easily the two classes—colon malignancy and normal tissue—separate into two distinct clusters. Despite the fact that we don't know the peptides' sequences, procedures of the invention are clear and robust and easily checked visually and statistically.

It will be understood to those of skill in the art that the methods of the invention assume little or nothing in particular about the type of disease being consider, and thus the invention can be implemented to develop a diagnostic tests very rapidly, e.g., in a matter of weeks.

In further embodiments, the invention has applications in conventional biomarker-based diagnostic and therapeutic applications. If one picks the largest principal component regions (Method II) one can then identify isotope clusters within them as cooperative biomarkers. If, as is often the case, a peptide resists identification, one can go down the list of statistically equivalent peptides until a successful identification is made. A single biomarker from an eigencomponent is a sufficient statistical representative.

Example Methods

As will be generally understood from the descriptions herein, in specific embodiments, the invention comprises a computer implemented method for determining a decision model that is then able to classifying a large data set (e.g., a biological data set produced by mass spectroscopy analysis) into one or more states that are also determined or trained by one or more large data sets, with the method generally as follows.

Acquire first and second training groups or sets of data arrays or images or maps. Align and normalizing using an image processing type algorithm, for example as described herein. Determine a differential image mask by comparing the aligned and normalized training images, thereby determining image pixel locations that are not useful in distinguishing between images in the first set or said second and storing results as a differential image mask. Applying the differential image mask to the training data to generate a filtered first set and a filtered second set of training data images. Expressing the filtered first set and second set of data images as a first set and second set of vectors in a basis of most significant principal components of the pixel values' covariance matrix, wherein the matrix expresses covariance between pixels' expression levels across said filtered first set and said filtered second set of data images. Selecting a decision procedure based on relative distribution and separability of said first set and second set of vectors. Applying the decision procedure to an unclassified data image to determine if said image is in said first state or said second state and outputting a result indicating whether unclassified data image is in said first state or said second state.

Embodiment in a Programmed Information Appliance

Figure 9:
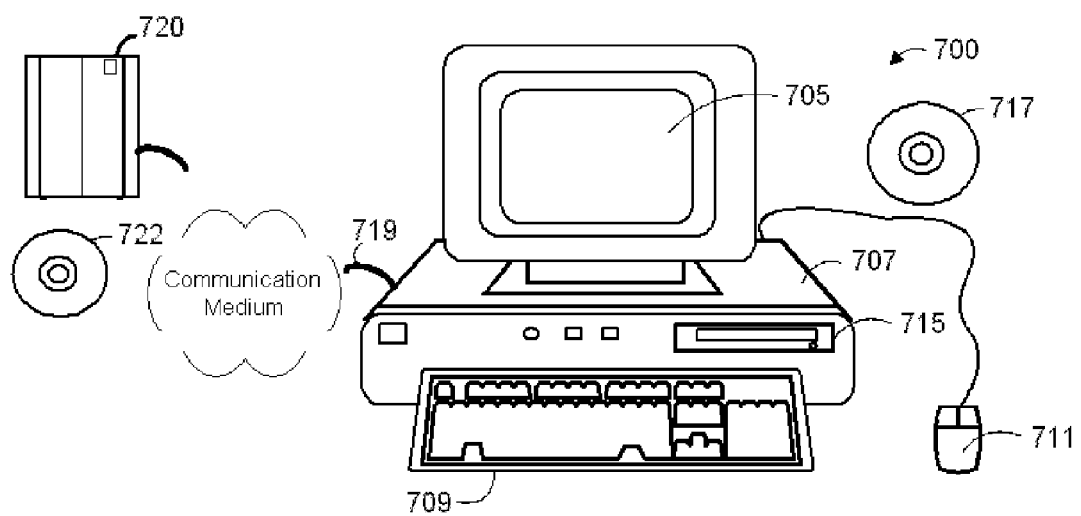
FIG. 9 is a block diagram showing a representative example logic device in which various aspects of the present invention may be implement and/or embodied.

FIG. 9 is a block diagram showing a representative example logic device in which various aspects of the present invention may be implement and/or embodied. As will be understood from the teachings provided herein, the invention can be implemented in hardware and/or software. In some embodiments, different aspects of the invention can be implemented in either client-side logic or server-side logic. Moreover, the invention or components thereof may be embodied in a fixed media program component containing logic instructions and/or data that when loaded into an appropriately configured computing device cause that device to perform according to the invention. A fixed media containing logic instructions may be delivered to a viewer on a fixed media for physically loading into a viewer's computer or a fixed media containing logic instructions may reside on a remote server that a viewer accesses through a communication medium in order to download a program component.

FIG. 9 shows an information appliance or digital device 700 that may be understood as a logical apparatus that can perform logical operations regarding image display and/or analysis as described herein. Such a device can be embodied as a general purpose computer system or workstation running logical instructions to perform according to specific embodiments of the present invention. Such a device can also be custom and/or specialized laboratory or scientific hardware that integrates logic processing into a machine for performing various sample handling operations. In general, the logic processing components of a device according to specific embodiments of the present invention is able to read instructions from media 717 and/or network port 719, which can optionally be connected to server 720 having fixed media 722. Apparatus 700 can thereafter use those instructions to direct actions or perform analysis as understood in the art and described herein. One type of logical apparatus that may embody the invention is a computer system as illustrated in 700, containing CPU 707, optional input devices 709 and 711, storage media (such as disk drives) 715 and optional monitor 705. Fixed media 717, or fixed media 722 over port 719, may be used to program such a system and may represent a disk-type optical or magnetic media, magnetic tape, solid state dynamic or static memory, etc. The invention may also be embodied in whole or in part as software recorded on this fixed media. Communication port 719 may also be used to initially receive instructions that are used to program such a system and may represent any type of communication connection.

According to specific embodiments of the invention, the invention can be implemented or understood as an information (or bioinformatics) logical pipeline for analyzing large data sets (such as proteomics data). Such a pipeline, as will be understood in the art, comprises a series of logical steps or executable logic modules or instructions, such as: a quantization logic module performing quantization of detector values into map images; an alignment logic module performing alignment of map images; a normalization logic module performing normalization of map images; a selection logic module for selecting differential signals of map images; a statistical data reduction module for simplifying data of map images; a discrimination module for discriminating between at least a first state and a second state of map images.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

Other Embodiments

The invention has now been described with reference to specific embodiments. Other embodiments will be apparent to those of skill in the art. In particular, an information appliance has generally been illustrated as a personal computer or workstation. However, the digital computing device is meant to be any information appliance suitable for performing the logic methods of the invention, and could include such devices as a digitally enabled laboratory systems or equipment, digitally enabled television, cell phone, personal digital assistant, etc. Modification within the spirit of the invention will be apparent to those skilled in the art. In addition, various different actions can be used to effect interactions with a system according to specific embodiments of the present invention. For example, a voice command may be spoken by an operator, a key may be depressed by an operator, a button on a client-side scientific device may be depressed by an operator, or selection using any pointing device may be effected by the user.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed is:

1. A computer implemented method for creating a decision model for classifying a biological data set produced by mass spectroscopy analysis, wherein said classifying comprises determining whether said biological data set is in a first state or a second state, said computer implemented method comprising:
    inputting a first training set of data into a computer, a plurality of said first set each derived from biological samples of a first state, said computer comprising at least a processor, data storage, an input module, and an output module;
    inputting a second training set of data into a said computer, a plurality of said second set each derived from biological samples of a second state;
    aligning and normalizing said first training set and said second training set using an image processing algorithm executing on said computer and storing in memory first and second aligned and normalized training images;
    deriving a differential image mask by comparing said first and second aligned and normalized training images using an image processing algorithm executing on said computer system, thereby determining image pixel locations that are not useful in distinguishing between said first set and said second set and storing results as a differential image mask in said computer;
    applying said differential image mask to generate a filtered first set and a filtered second set of data images using an image processing algorithm executing on said computer system;
    wherein a plurality of said images comprise an array of pixel values;
    expressing said filtered first set and second set of data images as a first set and second set of vectors in a basis of most significant principal components of said pixel values' covariance matrix, wherein said matrix expresses covariance between pixels' expression levels across said filtered first set and said filtered second set of data images and storing said first set and second set of vectors in said computer;
    using said computer system to select a decision procedure based on relative distribution and separability of said first set and second set of vectors;
    applying said decision procedure to an unclassified data image to determine if said image is in said first state or said second state;
    outputting a result indicating whether unclassified data image is in said first state or said second state.

2. The method according to claim 1 further wherein:
said filtered first set and said filtered second set of data images are sparse arrays of pixel values, said arrays comprising at least one dimension, said pixels comprising at least one distinguishable value.

3. The method according to claim 1 further wherein:
said sparse arrays are arrays of at least 2 dimensions.

4. The method according to claim 1 further comprising:
wherein said decision procedure comprises placing a test data in a first cluster or a second cluster when said relative distribution and separability of said first set and second set of vectors indicates at least a first cluster and a second cluster.

5. The method according to claim 1 further comprising:
wherein said expressing comprises:
determining significant eigen values and eigen vectors of a covariance matrix of said first set and second set of vectors.

6. The method according to claim 1 further wherein:
eignevalues and eignvectors are basis values of a coordinate set; and
expressing the sample images as vectors in the basis of most significant principal components of the pixels' covariance matrix.

7. The method according to claim 1 further comprising:
drawing a decision boundary in said reduced statistical space of eigenfeatures.

8. The method according to claim 1 further comprising:
expressing a plurality of said images in a data matrix, said matrix aligning pixel data from one image along a single axis (e.g., y) and said matrix aligning multiple images along a second axis (e.g., x);
applying an SVD algorithm, said algorithm presenting each sample image as a vector in the space of eigenvectors of the covariance matrix.

9. The method of claim 1 wherein said model analyzes one or more of: complex biological samples at the protein level, liquid-chromatography-mass-spectroscope (LC-MS) maps, mass-spectroscope data, complex satellite image data, complex MIR data, complex geologic, geographic, or astronomic map data.

10. A method for creating a decision model for classifying very large data sets (e.g., greater than about $10^7$ entries) as being of a first state or of a second state different than the first state, using a computer system, comprising:

obtaining a first set of data images, a plurality of said images each derived from a first state;

obtaining a second set of data images, a plurality of said images each derived from a second state;

aligning and normalizing data images in said first set and said second set using an image processing algorithm;

deriving a differential image mask by comparing images in said first set and said second set thereby determining image pixel locations that are not useful in distinguishing between said first set and said second set;

applying said differential image mask to generate a filtered first set and a filtered second set of data images;

wherein a plurality of said images comprise an array of pixel values;

expressing said filtered first set and second set of data images as a first set and second set of vectors in a basis of most significant principal components of said pixel values' covariance matrix, wherein said matrix expresses covariance between pixels' expression levels across said filtered first set and second set of data images; and selecting a decision procedure based on the relative distribution and separability of said first set and second set of vectors and;

classifying an unknown sample using said model, said classifying comprising:

obtaining an unclassified data image derived from an unclassified very large sample data set;

aligning and normalizing said unclassified data image such that said image is comparable with one or more images used to create said model using an image processing algorithm;

filtering said unclassified data image using said differential image;

expressing said filtered unclassified data image as a vector in the basis of most significant principal components of said model; and classifying said vector based on said vector's location (as denoted by its filtered, transformed and abbreviated coordinates) as compared with said first vector set and said second vector set;

outputting results of said classifying.

11. A method of analyzing liquid-chromatography-mass-spectroscope (LC-MS) maps using a computer system comprising:

transforming a plurality of raw LC-MS data sets maps using image processing techniques into a plurality of LC-MS images;

aligning said LC-MS images in LC retention time (RT) and mass-to-charge ratio (m/z) dimensions;

normalizing expression intensity levels of said LC-MS images;

filtering said LC-MS images by constructing and applying a series of binary masks corresponding to differential regions of various statistical significances between target and normal LC-MS images;

determining locations of target samples using map eigenfeatures;

differentiating between cancer and normal samples using a decision procedure; and outputting one or more data signals indicating whether a sample is cancerous or normal.

12. The method of claim 11 further comprising:
detecting statistical features of aligned LC-MS images to reduce the number of variables.

13. The method of claim 11 further comprising:
verifying internal consistency in alignment by performing commutativity tests on randomly selected triplets and quadruplets of maps;

wherein said transforming/quantizing comprises:
converting initial output data (e.g., original MS output WIFF files) into an array containing a plurality of sets of values of at least RT, m/z and intensity;

applying a cutoff to one or more of said values to reduce the number of sets in said array;

storing said reduced arrays;

selecting appropriate quantization scales so that scale(s) are small enough to make the image smooth in N-dimensional space and to reduce storage requirements, but not so small as to lose significant information;

aligning RT and m/z values across multiple samples;

aligning raw data directly by not assuming any functional form for the shifts from sample to sample, but allow them to vary in an arbitrary way and assuming that the deviations in m/z are relatively small compared to those in the RT dimension(s).

14. The methods of claim 11 further comprising:
differentially filtering said images by computing new pseudo-maps comprising:
disease mean,
disease deviation,
normal mean; and
normal deviation; and performing a pixel-by-pixel statistical operation producing at each pixel a mean or standard-deviation of corresponding log-normal pixels in disease and normal sets;

produce a fifth pseudo-map each pixel of which is the significance-test statistic of the disease and normal distributions for the corresponding pixels;

such that the intensity of the differential map is proportional to the level of statistical difference between the diseased and normal pixels in the collection.

15. A bioinformatics pipeline for analyzing proteomics data comprising:

a quantization logic module performing quantization of detector values into map images;

an alignment logic module performing alignment of map images;

a normalization logic module performing normalization of map images;

a selection logic module for selecting differential signals of map images;

a statistical data reduction module for simplifying data of map images;

a discrimination module for discriminating between at least a first state and a second state of map images, and a statistical feature detection logic module performing feature detection of map images.

* * * * *